US011021471B2

(12) United States Patent
Teng et al.

(10) Patent No.: US 11,021,471 B2
(45) Date of Patent: Jun. 1, 2021

(54) ANTIBACTERIAL COMPOUNDS

(71) Applicant: FORGE THERAPEUTICS, INC., San Diego, CA (US)

(72) Inventors: Min Teng, San Diego, CA (US); Baskar Nammalwar, San Diego, CA (US); Konstantin Taganov, San Diego, CA (US); Xiaoming Li, San Diego, CA (US); David T. Puerta, San Diego, CA (US)

(73) Assignee: FORGE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/612,308

(22) PCT Filed: May 9, 2018

(86) PCT No.: PCT/US2018/031896
§ 371 (c)(1),
(2) Date: Nov. 8, 2019

(87) PCT Pub. No.: WO2018/208985
PCT Pub. Date: Nov. 15, 2018

(65) Prior Publication Data
US 2020/0255413 A1 Aug. 13, 2020

Related U.S. Application Data

(60) Provisional application No. 62/504,218, filed on May 10, 2017.

(51) Int. Cl.
| C07D 405/14 | (2006.01) |
| C07D 309/40 | (2006.01) |
| C07D 405/06 | (2006.01) |
| C07D 405/12 | (2006.01) |
| C07D 407/04 | (2006.01) |
| C07D 413/10 | (2006.01) |
| C07D 471/04 | (2006.01) |
| C07D 487/04 | (2006.01) |
| C07D 493/04 | (2006.01) |
| A61P 31/04 | (2006.01) |

(52) U.S. Cl.
CPC ............ *C07D 405/14* (2013.01); *A61P 31/04* (2018.01); *C07D 309/40* (2013.01); *C07D 405/06* (2013.01); *C07D 405/12* (2013.01); *C07D 407/04* (2013.01); *C07D 413/10* (2013.01); *C07D 471/04* (2013.01); *C07D 487/04* (2013.01); *C07D 493/04* (2013.01)

(58) Field of Classification Search
CPC .. C07D 405/14; C07D 309/40; C07D 405/06; C07D 405/12; C07D 407/04; C07D 413/10; C07D 471/04; C07D 487/04; C07D 493/04; C07D 407/12; A61P 31/04
See application file for complete search history.

(56) References Cited

U.S. PATENT DOCUMENTS

| 5,543,534 A | 8/1996 | Vuligonda et al. |
| 5,846,514 A | 12/1998 | Foster et al. |
| 6,334,997 B1 | 1/2002 | Foster et al. |
| 7,579,486 B2 | 8/2009 | Puerta et al. |
| 7,786,316 B2 | 8/2010 | Puerta et al. |
| 9,145,381 B2 | 9/2015 | Fanelli et al. |
| 1,013,071 A1 | 11/2018 | Wong et al. |
| 1,041,473 A1 | 9/2019 | Teng et al. |
| 2003/0181472 A1 | 9/2003 | Clark et al. |
| 2003/0190608 A1 | 10/2003 | Blackburn |
| 2005/0009101 A1 | 1/2005 | Blackburn |
| 2007/0117848 A1 | 5/2007 | Puerta et al. |
| 2007/0149556 A1 | 6/2007 | Mikamiyama et al. |
| 2012/0035255 A1 | 2/2012 | Fanelli et al. |
| 2012/0041032 A1 | 2/2012 | Puerta et al. |
| 2012/0329741 A1 | 12/2012 | Oyelere et al. |
| 2014/0038990 A1 | 2/2014 | Buschmann et al. |
| 2014/0079666 A1 | 3/2014 | Webb et al. |
| 2015/0202208 A1 | 7/2015 | Kiyama et al. |
| 2017/0088532 A1 | 3/2017 | Cohen et al. |
| 2018/0319761 A1 | 11/2018 | Teng et al. |
| 2019/0106398 A1 | 4/2019 | Cohen et al. |
| 2020/0095236 A1 | 3/2020 | Teng et al. |

FOREIGN PATENT DOCUMENTS

| CN | 105777464 A | 7/2016 | |
| EP | 2181985 B1 * | 10/2011 | ............. A61P 31/12 |
| WO | WO-2004062601 A2 | 7/2004 | |
| WO | WO-2005110399 A2 | 11/2005 | |

(Continued)

OTHER PUBLICATIONS

Aytemir et al. Synthesis and Evaluation of Anticonvulsant and Antimicrobial Activities of 3-Hydroxy-6-methyl-2-substituted 4H-Pyran-4-one Derivatives. Archiv Der Pharmazie 337(5):281-288 (2004).
Berge et al. Pharmaceutical Salts. Journal of Pharmaceutical Sciences 66(1):1-19 (Jan. 1977).
Bingi et al. One-pot catalyst free synthesis of novel kojic acid tagged 2-aryl/alkyl substituted-4H-chromenes and evaluation of their antimicrobial and anti-biofilm activities. Bioorganic & Medicinal Chemistry Letters 25(9):1915-1919 (2015).
Bundgaard et al. Design of Prodrugs pp. 7-9, 21-24 (1985).
Co-pending U.S. Appl. No. 16/512,245, filed Jul. 15, 2019.
Di Francesco et al. Development of 2-t butyl-N-methyl pyrimidones as potent inhibitors of HIV integrase. Bioorg Med Chem Lett 18(8):2709-13 (2008).

(Continued)

*Primary Examiner* — John M Mauro
(74) *Attorney, Agent, or Firm* — Wilson Sonsini Goodrich & Rosati

(57) ABSTRACT

Provided herein are heterocyclic derivative compounds and pharmaceutical compositions comprising said compounds that are useful for inhibiting the growth of gram-negative bacteria. Furthermore, the subject compounds and compositions are useful for the treatment of bacterial infection, such as urinary tract infection and the like.

19 Claims, No Drawings

(56) References Cited

FOREIGN PATENT DOCUMENTS

| | | | |
|---|---|---|---|
| WO | WO-2006028523 A2 | 3/2006 |
| WO | WO-2008027466 A1 | 3/2008 |
| WO | WO-2008045668 A1 | 4/2008 |
| WO | WO-2008154642 A2 | 12/2008 |
| WO | WO-2010059838 A2 | 5/2010 |
| WO | WO-2010100475 A1 | 9/2010 |
| WO | WO-2012151567 A1 | 11/2012 |
| WO | WO-2012177638 A1 | 12/2012 |
| WO | WO-2013151923 A1 | 10/2013 |
| WO | WO-2014117090 A1 | 7/2014 |
| WO | WO-2014160649 A1 | 10/2014 |
| WO | WO-2015024010 A2 | 2/2015 |
| WO | WO-2015085238 A1 | 6/2015 |
| WO | WO-2015099107 A1 | 7/2015 |
| WO | WO-2017083431 A2 | 5/2017 |
| WO | WO-2017083434 A1 | 5/2017 |
| WO | WO-2018208985 A2 | 11/2018 |
| WO | WO-2018208987 A2 | 11/2018 |
| WO | WO-2020061375 A1 | 3/2020 |
| WO | WO-2020102572 A1 | 5/2020 |

OTHER PUBLICATIONS

Ding et al. Design, synthesis and biological evaluation of LpxC inhibitors with novel hydrophilic terminus. Chinese Chemical Letters 26(6):763-767 (2015).

Emami et al. Mannich bases of 7-piperazinylquinolones and kojic acid derivatives: Synthesis, in vitroantibacterial activity andin silicostudy. EP J Med Chem 68:185-191 (2010).

Evans. Synthesis of radiolabeled compounds. J Radioanal Chem 64(1-2):9-32 (1981).

Kabalka et al. The Synthesis of Radiolabeled Compounds via Organometallic Intermediates. Tetrahedron 45(21):6601-6621 (1989).

Krivonogov et al. Aminomethylation of pyrimidines. Russian Journal of Organic Chemistry 36(8):1219-1224 Chemical Abstracts CAS No. 345959-90-2P (2000).

Li et al. Design, synthesis and biological evaluation of 2-substituted 3-hydroxy-6-methyl-4H-pyran-4-one derivatives as Pseudomonas aeruginosa biofilm inhibitors. Eur J Med Chem 158:753-766 (2018).

Lin et al. Inhibition of LpxC protects mice from resistant Acinetobacter baumannii by modulating inflammation and enhancing phagocytosis. Mbio 3(5):pii:e00312-12 (2012).

Montgomery et al. Pyridone methylsulfone hydroxamate LpxC inhibitors for the treatment of serious gram-negative infections. J Med Chem 55:1662-1670 (2012).

PCT/US2016/061195 International Search Report and Written Opinion dated Jul. 31, 2017.

PCT/US2016/061198 International Search Report and Written Opinion dated Feb. 15, 2017.

PCT/US2018/031896 International Search Report and Written Opinion dated Nov. 7, 2018.

PCT/US2018/031898 International Search Report and Written Opinion dated Nov. 7, 2018.

Ravin. Chapter 76: Preforulation. Remington's Pharmaceutical Sciences, 17th ed., Mack Publishing Company, Easton, Pa. (pp. 1409-1423) (1985).

Storr et al., Vanadyl-thiazolidinedione combination agents for diabetes therapy. Bioconjugate Chemistry 14(1):212-221 (2003).

Us et al. 4H-Pyran-4-one derivatives:; leading molecule for preparation of compounds with antimycobacterial potential. Turkish Journal of Chemistry 30:803-812 (2009).

Us et al. Mannich base derivatives of 3-hydroxy-6- methyl-4H-pyran-4-one with antimicrobial activity. Turkish Journal of Chemistry 33:447-456 (2010).

Yan et al. Synthesis of hydroxypyrone- and hydroxythiopyrone-based matrix metalloproteinase inhibitors: Developing a structure-activity relationship. Bioorg. Med. Chem. Lett. 19(7):1970-1976 (2009).

PCT/US2019/061529 International Search Report and Written Opinion dated Mar. 13, 2020.

Hale et al. Exploring the UDP pocket of LpxC through amino acid analogs. Bioorg Med Chem Lett. 23:2362-2367 (2013).

PCT/US2019/052021 International Search Report and Written Opinion dated Jan. 6, 2020.

* cited by examiner

ANTIBACTERIAL COMPOUNDS

CROSS-REFERENCES TO RELATED APPLICATIONS

This application is filed pursuant to 35 U. SC. § 371 as a United States National Phase Application of International Application No. PCT/US2018/031896, filed May 9, 2018, which claims benefit of U.S. Patent Application No. 62/504,218, filed on May 10, 2017, all of which are hereby incorporated by reference in their entirety.

STATEMENT AS TO FEDERALLY SPONSORED RESEARCH

This invention was made with government support under IDSEP160030-03 awarded by the U.S. Department of Health & Human Services. The government has certain rights in the invention.

BACKGROUND

A need exists in the medicinal arts for the effective treatment of illness caused by bacterial infection.

BRIEF SUMMARY OF THE INVENTION

Provided herein are heterocyclic derivative compounds and pharmaceutical compositions comprising said compounds that are useful for inhibiting the growth of gram-negative bacteria. Furthermore, the subject compounds and compositions are useful for the treatment of bacterial infection, such as urinary tract infection and the like.

One embodiment provides a compound, or a pharmaceutically acceptable salt thereof, having the structure of Formula (I):

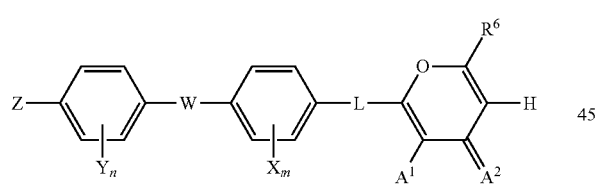

wherein,
n is 0, 1, or 2;
m is 0, 1, or 2;
$A^1$ is OH or SH;
$A^2$ is O or S;
L is selected from *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—;

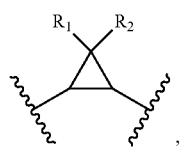

*—$N(R^5)$—$S(O)_2$—; *—$S(O)_2$—$N(R^5)$—, or wherein the * denotes a bond to the 4H-pyran-4-one ring or 4H-pyran-4-thione ring;

$R^1$, $R^3$, and $R^5$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_0$-$C_4$ alkylene)$N(R^{11})$—PO (optionally substituted $C_1$-$C_4$ alkyl)$_2$;

$R^2$ and $R^4$ are each independently H or optionally substituted $C_1$-$C_3$ alkyl;

$R^6$ is H, halogen, optionally substituted alkyl, hydroxyl, alkoxyl, cyano, amino, or nitro;

X is halogen or optionally substituted $C_1$-$C_3$ alkyl;
Y is halogen or optionally substituted $C_1$-$C_3$ alkyl;
W is a bond, —S—, —SO—, —$SO_2$—, —O—, —$CR^1R^3$—, —C(=$CR^1H$)—, *—$CR^1$=$CR^3$—; *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, wherein the * denotes a bond to the ring having the Y groups;

Z is H, -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$; L2 is a bond, optionally substituted $C_1$-$C_4$ alkylene, —C(O)—, or —$SO_2$—;

G is optionally substituted heterocyclyl, optionally substituted heteroaryl, —$N(R^{13})_2$, —$OR^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently selected from H or optionally substituted alkyl;

each $R^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^{14}$ is independently selected from H or optionally substituted alkyl;

provided that if $R^1$ if H, then $R^3$ or $R^5$ is not H; or if $R^3$ is H, then $R^1$ or $R^5$ is not H; and if W is a bond, then $R^1$ is not propyl, —$CH_2CH_2OH$, —$CH_2CH(OH)CH_2OH$.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$.

In other embodiments, $R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$.

In some embodiments, $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$.

In some embodiments, $R^2$, $R^4$, and $R^5$ are each independently H or optionally substituted $C_1$-$C_3$ alkyl. In certain embodiments, $R^2$ is H. In some embodiments, $R^1$ and $R^2$ are H. In further or additional embodiments, $R^3$ and $R^4$ are H. In some embodiments, n is 0. In other embodiments, n is 1 or 2. In some embodiments, m is 0. In other embodiments, m is 1 or 2. In certain embodiments, X is halogen. In some embodiments, Y is halogen. In some embodiments, Z is -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$. In some embodiments, W is a bond, or —C≡C—C≡C—. In certain embodiments, L is selected from *—$CR^1R^2$—$CR^3R^4$—; *—$CR^1R^2$—$N(R^5)$—; or *—C(O)—$N(R^5)$—. In certain embodiments, $R^6$ is H, $A^1$ is OH, and $A^2$ is O.

Provided herein in specific embodiments is a compound, or a pharmaceutically acceptable salt thereof, selected from:

3-hydroxy-2-(1-(methylsulfonyl)-2-(4-((4-(morpholinomethyl)phenyl)ethynyl)phenyl)ethyl)-4H-pyran-4-one;

3-hydroxy-4-oxo-N-(4-(phenylbuta-1,3-diyn-1-yl)phenyl)-4H-pyran-2-carboxamide;

N-(3-([1,1'-biphenyl]-4-yl)-2-(3-hydroxy-4-oxo-4H-pyran-2-yl)propyl)methanesulfonamide;

2-(1-([1,1'-biphenyl]-4-yl)-3-(methylsulfonyl)propan-2-yl)-3-hydroxy-4H-pyran-4-one;

2-(1-([1,1'-biphenyl]-4-yl)-3-hydroxypropan-2-yl)-3-hydroxy-4H-pyran-4-one; 2-(1-([1,1'-biphenyl]-4-yl)-3-aminopropan-2-yl)-3-hydroxy-4H-pyran-4-one; and 2-(([1,1'-biphenyl]-4-yl(2-hydroxyethyl)amino)methyl)-3-hydroxy-4H-pyran-4-one.

Also provided herein in specific embodiments is a compound, or a pharmaceutically acceptable salt thereof, selected from:

2-(1-(2-fluoroethylamino)-3-(4-(4-(morpholinomethyl)phenethyl)phenyl)propan-2-yl)-3-hydroxy-4H-pyran-4-one;

2-(1-(2-fluoroethylamino)-3-(4-(4-(morpholinomethyl)phenylthio)phenyl)propan-2-yl)-3-hydroxy-4H-pyran-4-one; and (E)-2-(1-(2-fluoroethylamino)-3-(4-(4-(morpholinomethyl)styryl)phenyl)propan-2-yl)-3-hydroxy-4H-pyran-4-one.

Some embodiments provided herein describe a compound, or a pharmaceutically acceptable salt thereof, having the structure of Formula (Ia):

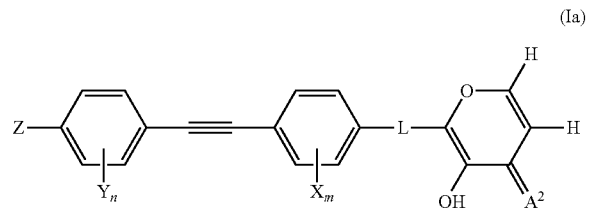

(Ia)

wherein,
n is 0, 1, or 2;
m is 0, 1, or 2;
$A^2$ is O or S;
L is selected from *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

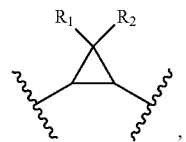

wherein the * denotes a bond to the 3-hydroxy-4H-pyran-4-one ring or 3-hydroxy-4H-pyran-4-thione ring;

$R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON($R^{11}$)$_2$, optionally substituted ($C_0$-$C_4$ alkylene)-CN, optionally substituted ($C_0$-$C_4$ alkylene)-OR$^{11}$, optionally substituted ($C_0$-$C_4$ alkylene)-N($R^{11}$)$_2$, optionally substituted ($C_0$-$C_4$ alkylene)N($R^{12}$)—COR$^{11}$, optionally substituted ($C_0$-$C_4$ alkylene)N($R^{12}$)—CO$_2R^{11}$, optionally substituted ($C_0$-$C_4$ alkylene)N($R^{12}$)—CON($R^{11}$)$_2$, optionally substituted ($C_0$-$C_4$ alkylene)-SO$_2$N($R^{11}$)$_2$, optionally substituted ($C_0$-$C_4$ alkylene)-SO$_2R^{11}$, optionally substituted ($C_0$-$C_4$ alkylene)N($R^{12}$)—SO$_2$N($R^{11}$)$_2$, optionally substituted ($C_0$-$C_4$ alkylene)N($R^{12}$)—SO$_2R^{11}$, optionally substituted ($C_0$-$C_4$ alkylene)-O—SO$_2$N($R^{11}$)$_2$, optionally substituted ($C_1$-$C_4$ alkylene)-N($R^{12}$)—SO$_2R^{11}$, optionally substituted ($C_1$-$C_4$ alkylene)-SO$_2R^{11}$, or optionally substituted ($C_0$-$C_4$ alkylene)N($R^{11}$)—PO (optionally substituted $C_1$-$C_4$ alkyl)$_2$;

$R^2$, $R^4$, and $R^5$ are each independently H or optionally substituted $C_1$-$C_3$ alkyl;

X is halogen or optionally substituted $C_1$-$C_3$ alkyl;

Y is halogen or optionally substituted $C_1$-$C_3$ alkyl;

Z is H, -L2-G, optionally substituted ($C_1$-$C_4$ alkylene)-OCON($R^{13}$)$_2$, optionally substituted ($C_1$-$C_4$ alkylene)-N($R^{14}$)CON($R^{13}$)$_2$, or optionally substituted ($C_1$-$C_4$ alkylene)-SO$_2$N($R^{13}$)$_2$;

L2 is a bond, optionally substituted $C_1$-$C_4$ alkylene, —C(O)—, or —SO$_2$—;

G is optionally substituted heterocyclyl, optionally substituted heteroaryl, —N($R^{13}$)$_2$, —OR$^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently selected from H or optionally substituted alkyl;

each $R^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^{14}$ is independently selected from H or optionally substituted alkyl;

provided that if $R^1$ if H, then $R^3$ is not H; or if $R^3$ is H, then $R^1$ is not H.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-OR11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In some embodiments, R1 is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In further embodiments, R3 is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In some embodiments, R2, R4, and R5 are each independently H or optionally substituted C1-C3 alkyl. In certain embodiments, R2 is H. In some embodiments, R1 and R2 are H. In further or additional embodiments, R3 and R4 are H. In some embodiments, n is 0. In other embodiments, n is 1 or 2. In some embodiments, m is 0. In other embodiments, m is 1 or 2. In certain embodiments, X is halogen. In some embodiments, Y is halogen. In some embodiments, Z is -L2-G, optionally substituted (C1-C4 alkylene)-OCON(R13)2, optionally substituted (C1-C4 alkylene)-N(R14)CON(R13)2, or optionally substituted (C1-C4 alkylene)-SO2N(R13)2. In certain embodiments, L is selected from *—CR1R2-CR3R4- or *—C(O)—N(R5)-. In certain embodiments, A2 is O.

Certain embodiments provided herein describe a compound, or a pharmaceutically acceptable salt thereof, having the structure of Formula (Ib):

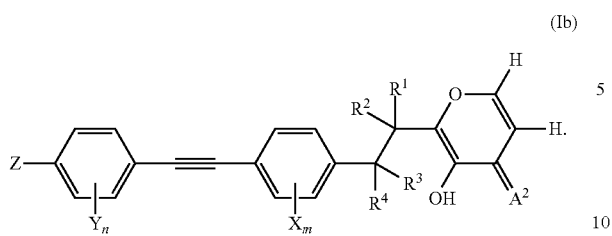

Certain specific embodiments provided herein describe a compound, or a pharmaceutically acceptable salt thereof, having the structure of Formula (Ic):

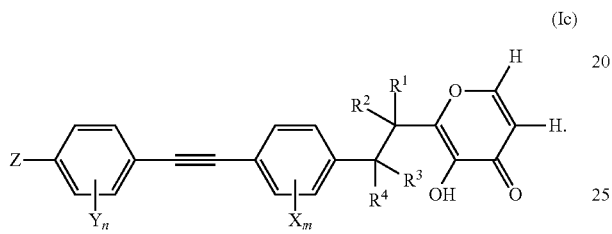

Other specific embodiments provided herein describe a compound, or a pharmaceutically acceptable salt thereof, having the structure of Formula (Id):

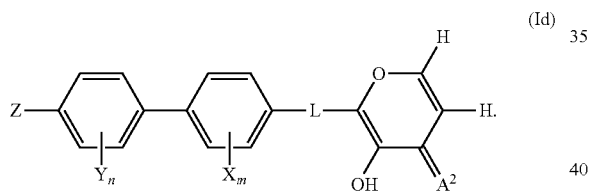

Provided herein in some embodiments, is a compound, or a pharmaceutically acceptable salt thereof, having the structure of formula (Id):

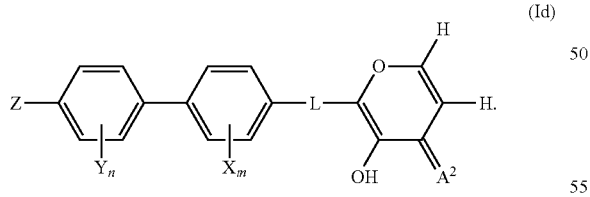

wherein, n is 0, 1, or 2;

m is 0, 1, or 2;

$A^2$ is O or S;

L is selected from *—$CR^1R^2$—$CR^3R^4$—; *—N($R^5$)—$CR^3R^4$—; *—$CR^1R^2$—N($R^5$)—; *—O—$CR^3R^4$—; *—$CR^1R^2$—O—; *—S—$CR^3R^4$—; *—$CR^1R^2$—S—; *—N($R^5$)—C(O)—; *—C(O)—N($R^5$)—; *—N($R^5$)—S(O)$_2$—; *—S(O)$_2$—N($R^5$)—, or

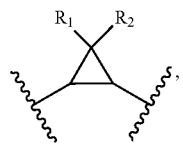

wherein the * denotes a bond to the 3-hydroxy-4H-pyran-4-one ring or 3-hydroxy-4H-pyran-4-thione ring;

$R^1$ and $R^3$ are each independently H, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-N($R^{11})_2$, optionally substituted ($C_0$-$C_4$ alkylene)N($R^{12}$)—$COR^{11}$, optionally substituted ($C_0$-$C_4$ alkylene)N($R^{12}$)—$CO_2R^{11}$, optionally substituted ($C_0$-$C_4$ alkylene)N($R^{12}$)—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)N($R^{12}$)—$SO_2N(R^{11})_2$, optionally substituted ($C_0$-$C_4$ alkylene)N($R^{12}$)—$SO_2R^{11}$, optionally substituted ($C_0$-$C_4$ alkylene)-O—$SO_2N(R^{11})_2$, optionally substituted ($C_1$-$C_4$ alkylene)-N($R^{12}$)—$SO_2R^{11}$, optionally substituted ($C_1$-$C_4$ alkylene)-$SO_2R^{11}$, or optionally substituted ($C_0$-$C_4$ alkylene)N($R^{11}$)—PO (optionally substituted $C_1$-$C_4$ alkyl)$_2$;

$R^2$, $R^4$, and $R^5$ are each independently H or optionally substituted $C_1$-$C_3$ alkyl;

X is halogen or optionally substituted $C_1$-$C_3$ alkyl;

Y is halogen or optionally substituted $C_1$-$C_3$ alkyl;

Z is H, -L2-G, optionally substituted ($C_1$-$C_4$ alkylene)-$OCON(R^{13})_2$, optionally substituted ($C_1$-$C_4$ alkylene)-N($R^{14}$)$CON(R^{13})_2$, or optionally substituted ($C_1$-$C_4$ alkylene)-$SO_2N(R^{13})_2$;

L2 is a bond, optionally substituted $C_1$-$C_4$ alkylene, —C(O)—, or —$SO_2$-;

G is optionally substituted heterocyclyl, optionally substituted heteroaryl, —N($R^{13})_2$, —$OR^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently selected from H or optionally substituted alkyl;

each $R^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^H$ is independently selected from H or optionally substituted alkyl.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In some embodiments, R1 is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In further embodiments, R3 is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In some embodiments, R2, R4, and R5 are each independently H or optionally substituted C1-C3 alkyl. In certain embodiments, R2 is H. In some embodiments, R1 and R2 are H. In further or additional embodiments, R3 and R4 are H. In some embodiments, n is 0. In other embodiments, n is 1 or 2. In some embodiments, m is 0. In other embodiments, m is 1 or 2. In certain embodiments, X is halogen. In some embodiments, Y is halogen. In some embodiments, Z is -L2-G, optionally substituted (C1-C4 alkylene)-OCON(R13)2, optionally substituted (C1-C4 alkylene)-N(R14)CON(R13)2, or optionally substituted (C1-C4 alkylene)-SO2N(R13)2. In certain embodiments, L is selected from *—CR1R2-CR3R4- or *—CR1R2-N(R5)- In certain embodiments, A2 is O.

Some embodiments provided herein describe a compound, or a pharmaceutically acceptable salt thereof, having the structure of Formula (II):

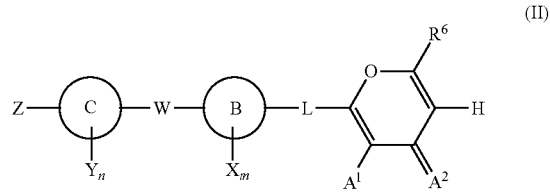

(II)

wherein,
n is 0, 1, or 2;
m is 0, 1, or 2;
$A^1$ is OH or SH;
$A^2$ is O or S;
L is selected from a bond, *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

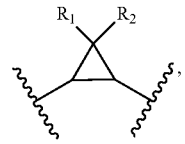

wherein the * denotes a bond to the 4H-pyran-4-one ring or 4H-pyran-4-thione ring;

$R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_0$-$C_4$ alkylene)$N(R^{11})$—PO (optionally substituted $C_1$-$C_4$ alkyl)$_2$;

$R^2$, $R^4$, and $R^5$ are each independently H or optionally substituted $C_1$-$C_3$ alkyl;

$R^6$ is H, halogen, optionally substituted alkyl, hydroxyl, alkoxyl, cyano, amino, or nitro;

B is phenyl,

[structures: pyridinone, pyridine, indazole, imidazopyridine, isoindolinone, 2H-indazole, indolizine, imidazopyrrolinone, methylenedioxy-benzofuran, benzofuran, dihydrobenzofuran]

, or ;

W is a bond, —S—, —SO—, —SO$_2$—, —O—, —CR'R$^3$—, —C(=CR$^1$H)—, *—CR$^1$=CR$^3$—; *—CR$^1$R$^2$—CR$^3$R$^4$—; *—N(R$^5$)—CR$^3$R$^4$—; *—CR$^1$R$^2$—N(R$^5$)—; *—O—CR$^3$R$^4$—; *—CR$^1$R$^2$—O—; *—S—CR$^3$R$^4$—; *—CR$^1$R$^2$—S—; *—N(R$^5$)—C(O)—; *—C(O)—N(R$^5$)—; *—N(R$^5$)—S(O)$_2$—; *—S(O)$_2$—N(R$^5$)—, wherein the * denotes a bond to the ring having the Y groups;

C is phenyl, cycloalkyl,

[structures: pyridinone, pyridine, indazole, imidazopyridine, isoindolinone, 2H-indazole, indolizine, imidazopyrrolinone, methylenedioxy-benzofuran, benzofuran, dihydrobenzofuran]

, or ;

provided that if

B is phenyl, then

C is not phenyl; and if

C is phenyl, then

B is not phenyl;

X is halogen or optionally substituted C$_1$-C$_3$ alkyl;
Y is halogen or optionally substituted C$_1$-C$_3$ alkyl;
Z is H, -L2-G, optionally substituted (C$_1$-C$_4$ alkylene)-OCON(R$^{13}$)$_2$, optionally substituted (C$_1$-C$_4$ alkylene)-N(R$^{14}$)CON(R$^{13}$)$_2$, or optionally substituted (C$_1$-C$_4$ alkylene)-SO$_2$N(R$^{13}$)$_2$;

L2 is a bond, optionally substituted C₁-C₄ alkylene, —C(O)—, or —SO₂—;
G is optionally substituted heterocyclyl, optionally substituted heteroaryl, —N(R¹³)₂, —OR¹³, halogen, or —CN;
each R¹¹ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two R¹¹ groups together with the nitrogen to which they are attached join to form an optionally substituted N-heterocyclyl;
each R¹² is independently selected from H or optionally substituted alkyl;
each R¹³ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two R¹³ groups together with the nitrogen to which they are attached join to form an optionally substituted N-heterocyclyl; and
each R¹⁴ is independently selected from H or optionally substituted alkyl.

In some embodiments, R¹ and R³ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In some embodiments, R1 is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In further embodiments, R3 is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR11, —CON(R11)2, optionally substituted (C1-C4 alkylene)-CN, optionally substituted (C1-C4 alkylene)-0R11, optionally substituted (C1-C4 alkylene)-N(R11)2, optionally substituted (C1-C4 alkylene)N(R12)-COR11, optionally substituted (C1-C4 alkylene)N(R12)-CO2R11, optionally substituted (C1-C4 alkylene)N(R12)-CON(R11)2, optionally substituted (C1-C4 alkylene)N(R12)-SO2N(R11)2, optionally substituted (C1-C4 alkylene)-O—SO2N(R11)2, optionally substituted (C1-C4 alkylene)-N(R12)-SO2R11, optionally substituted (C1-C4 alkylene)-SO2R11, or optionally substituted (C1-C4 alkylene)N(R11)-PO (optionally substituted C1-C4 alkyl)2.

In some embodiments, R2, R4, and R5 are each independently H or optionally substituted C1-C3 alkyl. In certain embodiments, R2 is H. In some embodiments, R1 and R2 are H. In further or additional embodiments, R3 and R4 are H. In some embodiments, n is 0. In other embodiments, n is 1 or 2. In some embodiments, m is 0. In other embodiments, m is 1 or 2. In certain embodiments, X is halogen. In some embodiments, Y is halogen. In some embodiments, Z is -L2-G, optionally substituted (C1-C4 alkylene)-OCON(R13)2, optionally substituted (C1-C4 alkylene)-N(R14)CON(R13)2, or optionally substituted (C1-C4 alkylene)-SO2N(R13)2. In certain embodiments, W is a bond, or —C≡C—C≡C—. In some embodiments, W is —C≡C—, or —C≡C—C≡C—. In some embodiments, *—CR1R2-CR3R4-; *—CR1R2-N(R5)-; or *—C(O)—N(R5)-. In certain embodiments, R6 is H, A1 is OH, and A2 is O.

In some embodiments,

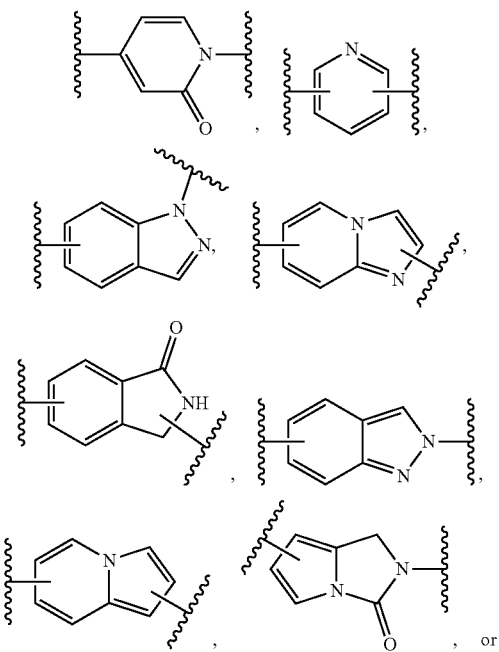

is phenyl,

-continued

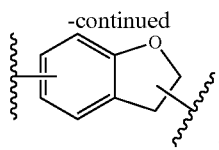

In certain embodiments,

Ⓒ is phenyl, cycloalkyl,

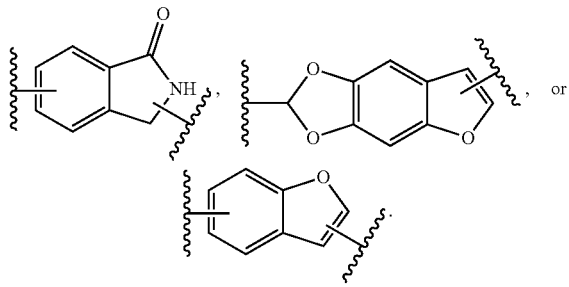

In certain specific embodiments,

Ⓒ is phenyl or cyclopropyl.

Provided herein in specific embodiments is a compound, or a pharmaceutically acceptable salt thereof, selected from:
2-(1-(4-(benzofuro[6,5-d][1,3]dioxol-6-yl)phenyl)-3-(2-fluoroethylamino)propan-2-yl)-3-hydroxy-4H-pyran-4-one;
2-(1-(4-(benzofuran-2-yl)phenylthio)-2-(2-fluoroethylamino)ethyl)-3-hydroxy-4H-pyran-4-one;
N-(2-fluoroethyl)-2-(3-hydroxy-4-oxo-4H-pyran-2-yl)-3-(6-(4-(2-hydroxyethyl)phenyl)-3-oxo-1H-pyrrolo[1,2-c]imidazol-2(3H)-yl)propanamide;
2-(1-(5-(cyclopropylethynyl)-2H-indazol-2-yl)-3-(2-fluoroethylamino)propan-2-yl)-3-hydroxy-4H-pyran-4-one;
2-(1-(6-(cyclopropylethynyl)imidazo[1,2-a]pyridin-2-yl)-3-(2-fluoroethylamino)propan-2-yl)-3-hydroxy-4H-pyran-4-one;
2-(1-(5-(cyclopropylbuta-1,3-diynyl)-1H-indazol-1-yl)-3-(2-fluoroethylamino)propan-2-yl)-3-hydroxy-4H-pyran-4-one;
5-(cyclopropylethynyl)-2-(3-(2-fluoroethylamino)-2-(3-hydroxy-4-oxo-4H-pyran-2-yl)propyl)isoindolin-1-one;
2-(1-(6-(cyclopropylethynyl)indolizin-2-yl)-3-(2-fluoroethylamino)propan-2-yl)-3-hydroxy-4H-pyran-4-one;
3-hydroxy-2-(6-(phenylethynyl)-2,3-dihydrobenzofuran-2-yl)-4H-pyran-4-one;
N-(2,2-difluoroethyl)-3-(4-((4-(1,2-dihydroxyethyl)phenyl)ethynyl)-2-oxopyridin-1(2H)-yl)-2-(3-hydroxy-4-oxo-4H-pyran-2-yl)propanamide; and
5-(6-(3-(2-fluoroethylamino)-2-(3-hydroxy-4-oxo-4H-pyran-2-yl)propyl)pyridin-3-yl)isoindolin-1-one.

Some embodiments provided herein describe a pharmaceutical composition comprising a compound of Formula (I), (Ia), (Ib), (Ic), (Id), or (II), or a pharmaceutically acceptable salt thereof, and a pharmaceutically acceptable excipient.

Other embodiments provided herein describe a method of inhibiting UDP-{3-O—[(R)-3-hydroxymyristoyl]}-N-acetylglucosamine deacetylase enzyme comprising contacting the enzyme with a compound of Formula (I), (Ia), (Ib), (Ic), (Id), or (II).

Also provided herein in certain embodiments is a method for treating bacterial infection in a patient in need thereof comprising administering to the patient a composition comprising a compound of Formula (I), (Ia), (Ib), (Ic), (Id), or (II), or a pharmaceutically acceptable salt thereof, and a pharmaceutically acceptable excipient.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.
"Amino" refers to the —NH2 radical.
"Cyano" refers to the —CN radical.
"Nitro" refers to the —NO2 radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH2 radical.
"Alkyl" refers to a straight or branched hydrocarbon chain radical consisting solely of carbon and hydrogen atoms, containing no unsaturation, having from one to fifteen carbon atoms (e.g., C1-C15 alkyl). In certain embodiments, an alkyl comprises one to thirteen carbon atoms (e.g., C1-C13 alkyl). In certain embodiments, an alkyl comprises one to eight carbon atoms (e.g., C1-C8 alkyl). In other embodiments, an alkyl comprises one to five carbon atoms (e.g., C1-C5 alkyl). In other embodiments, an alkyl comprises one to four carbon atoms (e.g., C1-C4 alkyl). In other embodiments, an alkyl comprises one to three carbon atoms (e.g., C1-C3 alkyl). In other embodiments, an alkyl comprises one to two carbon atoms (e.g., C1-C2 alkyl). In other embodiments, an alkyl comprises one carbon atom (e.g., C1 alkyl). In other embodiments, an alkyl comprises five to fifteen carbon atoms (e.g., C5-C15 alkyl). In other embodiments, an alkyl comprises five to eight carbon atoms (e.g., C5-C8 alkyl). In other embodiments, an alkyl comprises two to five carbon atoms (e.g., C2-C5 alkyl). In other embodiments, an alkyl comprises three to five carbon atoms (e.g., C3-C5 alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —ORa, —SRa, —OC(O)-Ra, —N(Ra)2, —C(O)Ra, —C(O)ORa, —C(O)N(Ra)2, —N(Ra)C(O)ORa, —OC(O)—N(Ra)$_2$, —N(Ra)C(O)Ra, —N(Ra)S(O)tRa (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —ORa, —SRa, —OC(O)-Ra, —N(Ra)2, —C(O)Ra, —C(O)ORa, —C(O)N(Ra)2, —N(Ra)C(O)ORa, —OC(O)—N(Ra)$_2$, —N(Ra)C(O)Ra, —N(Ra)S(O)tRa (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —ORa, —SRa, —OC(O)-Ra, —N(Ra)2, —C(O)Ra, —C(O)ORa, —C(O)N(Ra)2, —N(Ra)C(O)ORa, —OC(O)—N(Ra)2, —N(Ra)C(O)Ra, —N(Ra)S(O)tRa (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., C1-C8 alkylene). In other embodiments, an alkylene comprises one to five carbon atoms (e.g., C1-C5 alkylene). In other embodiments, an alkylene comprises one to four carbon atoms (e.g., C1-C4 alkylene). In other embodiments, an alkylene comprises one to three carbon atoms (e.g., C1-C3 alkylene). In other embodiments, an alkylene comprises one to two carbon atoms (e.g., C1-C2 alkylene). In other embodiments, an alkylene comprises one carbon atom (e.g., C1 alkylene). In other embodiments, an alkylene comprises five to eight carbon atoms (e.g., C5-C8 alkylene). In other embodiments, an alkylene comprises two to five carbon atoms (e.g., C2-C5 alkylene). In other embodiments, an alkylene comprises three to five carbon atoms (e.g., C3-C5 alkylene). Unless stated otherwise specifically in the specification, an alkylene chain is optionally substituted by one or more of the following substituents: halo, cyano, nitro, oxo, thioxo, imino, oximo, trimethylsilanyl, —ORa, —SRa, —OC(O)-Ra, —N(Ra)2, —C(O)Ra, —C(O)ORa, —C(O)N(Ra)2, —N(Ra)C(O)ORa, —OC(O)—N(Ra)2, —N(Ra)C(O)Ra, —N(Ra)S(O)tRa (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., C2-C8 alkenylene). In other embodiments, an alkenylene comprises two to five carbon atoms (e.g., C2-C5 alkenylene). In other embodiments, an alkenylene comprises two to four carbon atoms (e.g., C2-C4 alkenylene). In other embodiments, an alkenylene comprises two to three carbon atoms (e.g., C2-C3 alkenylene). In other embodiments, an alkenylene comprises five to eight carbon atoms (e.g., C5-C8 alkenylene). In other embodiments, an alkenylene comprises two to five carbon atoms (e.g., C2-C5 alkenylene). In other embodiments, an alkenylene comprises three to five carbon atoms (e.g., C3-C5 alkenylene). Unless stated otherwise specifically in the specification, an alkenylene chain is optionally substituted by one or more of the following substituents: halo, cyano, nitro, oxo, thioxo, imino, oximo, trimethylsilanyl, —ORa, —SRa, —OC(O)-Ra, —N(Ra)2, —C(O)Ra, —C(O)ORa, —C(O)N(Ra)2, —N(Ra)C(O)ORa, —OC(O)—N(Ra)2, —N(Ra)C(O)Ra, —N(Ra)S(O)tRa (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., C2-C8 alkynylene). In other embodiments, an alkynylene comprises two to five carbon atoms (e.g., C2-C5 alkynylene). In other embodiments, an alkynylene comprises two to four carbon atoms (e.g., C2-C4 alkynylene). In other embodiments, an alkynylene comprises two to three carbon atoms (e.g., C2-C3 alkynylene). In other embodiments, an alkynylene comprises two carbon atom (e.g., C2 alkylene). In other embodiments, an alkynylene comprises five to eight carbon atoms (e.g., C5-C8 alkynylene). In other embodiments, an alkynylene comprises three to five carbon atoms (e.g., C3-C5 alkynylene). Unless stated otherwise specifically in the specification, an alkynylene chain is optionally substituted by one or more of the following substituents: halo, cyano, nitro, oxo, thioxo, imino, oximo, trimethylsilanyl, —ORa, —SRa, —OC(O)—Ra, —N(Ra)2, —C(O)Ra, —C(O)ORa, —C(O)N(Ra)2, —N(Ra)C(O)ORa, —OC(O)—N(Ra)2, —N(Ra)C(O)Ra, —N(Ra)S(O)tRa (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —Rb-ORa, —Rb-OC(O)—Ra, —Rb-OC(O)—ORa, —Rb-OC(O)—N(Ra)$_2$, —Rb-N(Ra)$_2$, —Rb-C(O)Ra, —Rb-C(O)ORa, —Rb-C(O)N(Ra)$_2$, —Rb-O—Rc-C(O)N(Ra)$_2$, —Rb-N(Ra)C(O)ORa, —Rb-N(Ra)C(O)Ra, —Rb-N(Ra)S(O)tRa (where t is 1 or 2), —Rb-S(O)tRa (where t is 1 or 2), —Rb-S(O)tORa (where t is 1 or 2) and —Rb-S(O)tN(Ra)$_2$ (where t is 1 or 2), where each Ra is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each Rb is independently a direct bond or a straight or branched alkylene or alkenylene chain, and Rc is a straight or branched alkylene or alkenylene chain, and where each of the above substituents is unsubstituted unless otherwise indicated.

"Aralkyl" refers to a radical of the formula —Rc-aryl where Rc is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —Rd-aryl where Rd is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —Re-aryl, where Re is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—Rc-aryl where Rc is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —Rb-ORa, —Rb-OC(O)-Ra, —Rb-OC(O)—ORa, —Rb-OC(O)—N(Ra)$_2$, —Rb-N(Ra)$_2$, —Rb-C(O)Ra, —Rb-C(O)ORa, —Rb-C(O)N(Ra)$_2$, —Rb-O—Rc-C(O)N(Ra)$_2$, —Rb-N(Ra)C(O)ORa, —Rb-N(Ra)C(O)Ra, —Rb-N(Ra)S(O)tRa (where t is 1 or 2), —Rb-S(O)tRa (where t is 1 or 2), —Rb-S(O)tORa (where t is 1 or 2) and —Rb-S(O)tN(Ra)$_2$ (where t is 1 or 2), where each Ra is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each Rb is independently a direct bond or a straight or branched alkylene or alkenylene chain, and Rc is a straight or branched alkylene or alkenylene chain, and where each of the above substituents is unsubstituted unless otherwise indicated.

"Carbocyclylalkyl" refers to a radical of the formula —Rc-carbocyclyl where Rc is an alkylene chain as defined above. The alkylene chain and the carbocyclyl radical are optionally substituted as defined above.

"Carbocyclylalkynyl" refers to a radical of the formula —Rc-carbocyclyl where Rc is an alkynylene chain as defined above. The alkynylene chain and the carbocyclyl radical are optionally substituted as defined above.

"Carbocyclylalkoxy" refers to a radical bonded through an oxygen atom of the formula —O—Rc-carbocyclyl where Rc is an alkylene chain as defined above. The alkylene chain and the carbocyclyl radical are optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

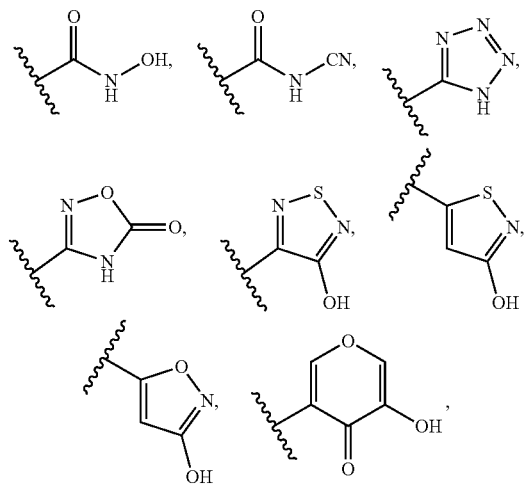

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —Rb-ORa, —Rb-OC(O)-Ra, —Rb-OC(O)—ORa, —Rb-OC(O)—N(Ra)$_2$, —Rb-N(Ra)$_2$, —Rb-C(O)Ra, —Rb-C(O)ORa, —Rb-C(O)N(Ra)$_2$, —Rb-O—Rc-C(O)N(Ra)$_2$, —Rb-N(Ra)C(O)ORa, —Rb-N(Ra)C(O)Ra, —Rb-N(Ra)S(O)tRa (where t is 1 or 2), —Rb-S(O)tRa (where t is 1 or 2), —Rb-S(O)tORa (where t is 1 or 2) and -Rb-S(O)tN(Ra)$_2$ (where t is 1 or 2), where each Ra is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each Rb is independently a direct bond or a straight or branched alkylene or alkenylene chain, and Rc is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —Rc-heterocyclyl where Rc is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—Rc-heterocyclyl where Rc is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahy drobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —Rb-ORa, —Rb-OC(O)-Ra, —Rb-OC(O)—ORa, —Rb-OC(O)—N(Ra)2, —Rb-N(Ra)2, —Rb-C(O)Ra, —Rb-C(O)ORa, —Rb-C(O)N(Ra)2, —Rb-O—Rc-C(O)N(Ra)2, —Rb-N(Ra)C(O)ORa, —Rb-N(Ra)C(O)Ra, —Rb-N(Ra)S(O)tRa (where t is 1 or 2), —Rb-S(O)tRa (where t is 1 or 2), —Rb-S(O)tORa (where t is 1 or 2) and -Rb-S(O)tN(Ra)2 (where t is 1 or 2), where each Ra is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each Rb is independently a direct bond or a straight or branched alkylene or alkenylene chain, and Rc is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —Rc-heteroaryl, where Rc is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—Rc-heteroaryl, where Rc is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

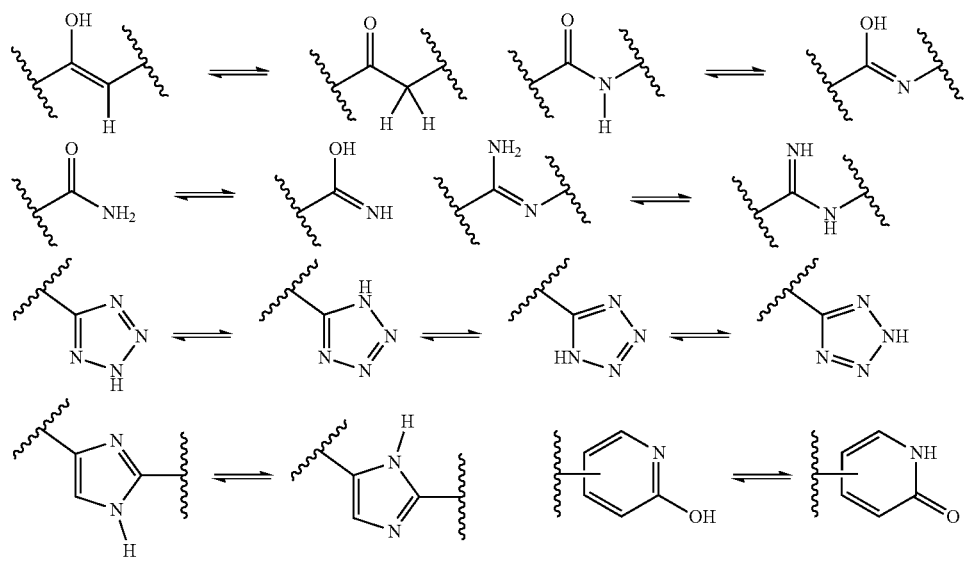

The compounds disclosed herein, in some embodiments, are used in different enriched isotopic forms, e.g., enriched in the content of 2H, 3H, 11C, 13C and/or 14C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium (2H), tritium (3H), iodine-125 (125I) or carbon-14 (14C). Isotopic substitution with 2H, 11C, 13C, 14C, 15C, 12N, 13N, 15N, 16N, 16O, 17O, 14F, 15F, 16F, 17F, 18F, 33S, 34S, 35S, 36S, 35Cl, 37Cl, 79Br, 81Br, 125I are all contemplated. All isotopic variations of the compounds of the present invention, whether radioactive or not, are encompassed within the scope of the present invention.

In certain embodiments, the compounds disclosed herein have some or all of the 1H atoms replaced with 2H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d3 (CD3I), are readily available and may be employed to transfer a deuterium-substituted carbon atom under nucleophilic substitution reaction conditions to the reaction substrate. The use of CD$_3$I is illustrated, by way of example only, in the reaction schemes below.

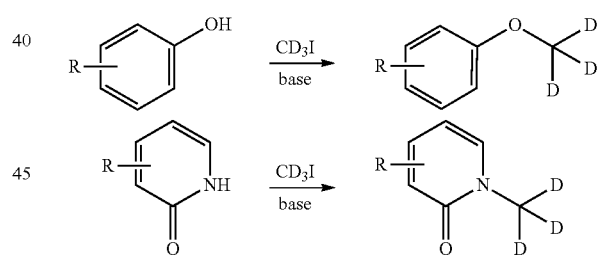

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

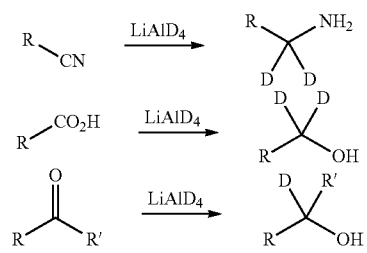

Deuterium gas and palladium catalyst are employed to reduce unsaturated carbon-carbon linkages and to perform a reductive substitution of aryl carbon-halogen bonds as illustrated, by way of example only, in the reaction schemes below.

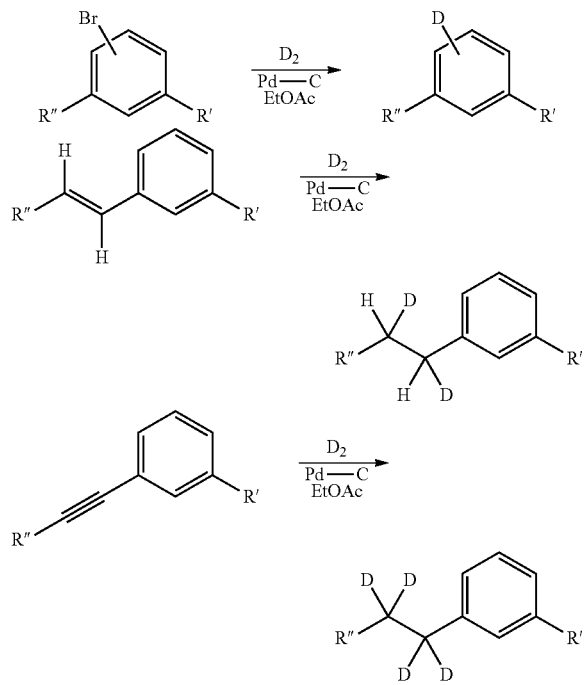

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the heterocyclic LpxC inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

LpxC Inhibitory Compounds

Provided herein are heterocyclic LpxC inhibitory compounds and pharmaceutical compositions comprising said compounds. The subject compounds and compositions are useful for inhibiting UDP-{3-O—[(R)-3-hydroxymyristoyl]}-N-acetylglucosamine deacetylase (LpxC) and for the treatment of bacterial infection.

One embodiment provides a compound, or a pharmaceutically acceptable salt thereof, having the structure of Formula (I):

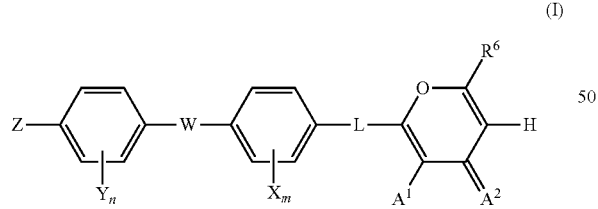

wherein, n is 0, 1, or 2;

m is 0, 1, or 2;

$A^1$ is OH or SH;

$A^2$ is O or S;

L is selected from *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

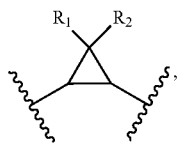

wherein the * denotes a bond to the 4H-pyran-4-one ring or 4H-pyran-4-thione ring;

$R^1$, $R^3$, and $R^5$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_0$-$C_4$ alkylene)-$N(R^{12})$—$SO_2R^{11}$, optionally substituted ($C_1$-$C_4$ alkylene)-$SO_2R^{11}$, or optionally substituted ($C_0$-$C_4$ alkylene)$N(R^{11})$—PO (optionally substituted $C_1$-$C_4$ alkyl)$_2$;

$R^2$ and $R^4$ are each independently H or optionally substituted $C_1$-$C_3$ alkyl;

$R^6$ is H, halogen, optionally substituted alkyl, hydroxyl, alkoxyl, cyano, amino, or nitro;

X is halogen or optionally substituted $C_1$-$C_3$ alkyl;

Y is halogen or optionally substituted $C_1$-$C_3$ alkyl;

W is a bond, —S—, —SO—, —$SO_2$—, —O—, —$CR'R^3$—, —C(=$CR^1H$)—, *—$CR^1$=$CR^3$—; *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, wherein the * denotes a bond to the ring having the Y groups;

Z is H, -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$;

L2 is a bond, optionally substituted $C_1$-$C_4$ alkylene, —C(O)—, or —$SO_2$—;

G is optionally substituted heterocyclyl, optionally substituted heteroaryl, —$N(R^{13})_2$, —$OR^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently selected from H or optionally substituted alkyl;

each $R^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^{14}$ is independently selected from H or optionally substituted alkyl;

provided that if $R^1$ if H, then $R^3$ or $R^5$ is not H; or if $R^3$ is H, then $R^1$ or $R^5$ is not H; and if W is a bond, then $R^1$ is not propyl, —$CH_2CH_2OH$, —$CH_2CH(OH)CH_2OH$.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In some embodiments, $R^1$ and $R^3$ are each independently H, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^1$ and $R^3$ are each independently H, ($C_1$-$C_4$ alkylene)-OH, ($C_1$-$C_4$ alkylene)-$NH_2$, ($C_1$-$C_4$ alkylene)-NH—$SO_2Me$, or ($C_1$-$C_4$ alkylene)-$SO_2Me$.

In some embodiments, $R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In other embodiments, $R^1$ is optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^1$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2Me$, or optionally substituted ($C_1$-$C_4$ alkylene)-$SO_2Me$.

In some embodiments, $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In other embodiments, $R^3$ is optionally substituted ($C_1$-$C_4$ alkylene)-$OR^{11}$, optionally substituted ($C_1$-$C_4$ alkylene)-N($R^{11}$)$_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^3$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2Me$, or optionally substituted ($C_1$-$C_4$ alkylene)-$SO_2Me$.

In some embodiments, $R^2$, $R^4$, and $R^5$ are each independently H or optionally substituted $C_1$-$C_3$ alkyl. In some embodiments, $R^2$ is H. In some embodiments, $R^4$ is H. In some embodiments, $R^5$ is H. In some embodiments, $R^2$, $R^4$, and $R^5$ are H. In some embodiments, $R^1$ and $R^2$ are H. In some embodiments, $R^3$ and $R^4$ are H.

In some embodiments, n is 0. In some embodiments, m is 0. In some embodiments, m is 1 or 2. In some embodiments, m is 1. In some embodiments, m is 2. In some embodiments, n is 1 or 2. In some embodiments, n is 1. In some embodiments, n is 2. In some embodiments, X is halogen. In some embodiments, X is F. In some embodiments, Y is halogen. In some embodiments, Y is F.

In some embodiments, Z is -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$. In some embodiments, Z is H or -L2-G, wherein L2 is $C_1$-$C_4$ alkylene and G is optionally substituted heterocyclyl. In some embodiments, Z is H. In some embodiments, Z is L2-G, wherein L2 is $C_1$-$C_4$ alkylene and G is optionally substituted heterocyclyl.

In some embodiments, W is a bond, or —C≡C—C≡C—. In other embodiments, W is a —C≡C— or —C≡C—C≡C—. In some embodiments, W is a bond.

In some embodiments, L is *—$CR^1R^2$—$CR^3R^4$—; *—$CR^1R^2$—$N(R^5)$—; or *—C(O)—$N(R^5)$—. In some embodiments, L is *—$CR^1R^2$—$CR^3R^4$— or *—$CR^1R^2$—$N(R^5)$—. In some embodiments, L is *—$CR^1R^2$—$CR^3R^4$— or *—C(O)—$N(R^5)$—. In some embodiments, L is *—$CR^1R^2$—$CR^3R^4$—. In some embodiments, L is *—$CR^1R^2$—$N(R^5)$—. In some embodiments, L is *—C(O)—$N(R^5)$—.

In some embodiments, $R^6$ is H, F, $C_1$, Br, alkyl, hydroxyl, alkoxyl, cyano, amino, or nitro. In some embodiments, $R^6$ is H.

In some embodiments, $A^1$ is OH and $A^2$ is O. In some embodiments, $A^1$ is SH and $A^2$ is O. In some embodiments, $A^1$ is SH and $A^2$ is S. In some embodiments, $A^1$ is OH and $A^2$ is S.

In certain embodiments, a compound of Formula (I) is a compound selected from:

3-hydroxy-2-(1-(methylsulfonyl)-2-(4-((4-(morpholinomethyl)phenyl)ethynyl)phenyl)ethyl)-4H-pyran-4-one;

3-hydroxy-4-oxo-N-(4-(phenylbuta-1,3-diyn-1-yl)phenyl)-4H-pyran-2-carboxamide;

N-(3-([1,1'-biphenyl]-4-yl)-2-(3-hydroxy-4-oxo-4H-pyran-2-yl)propyl)methanesulfonamide;

2-(1-([1,1'-biphenyl]-4-yl)-3-(methylsulfonyl)propan-2-yl)-3-hydroxy-4H-pyran-4-one;

2-(1-([1,1'-biphenyl]-4-yl)-3-hydroxypropan-2-yl)-3-hydroxy-4H-pyran-4-one;

2-(1-([1,1'-biphenyl]-4-yl)-3-aminopropan-2-yl)-3-hydroxy-4H-pyran-4-one;

2-(([1,1'-biphenyl]-4-yl(2-hydroxyethyl)amino)methyl)-3-hydroxy-4H-pyran-4-one.

2-(1-(2-fluoroethylamino)-3-(4-(4-(morpholinomethyl)phenethyl)phenyl)propan-2-yl)-3-hydroxy-4H-pyran-4-one;

2-(1-(2-fluoroethylamino)-3-(4-(4-(morpholinomethyl)phenylthio)phenyl)propan-2-yl)-3-hydroxy-4H-pyran-4-one; or (E)-2-(1-(2-fluoroethylamino)-3-(4-(4-(morpholinomethyl)styryl)phenyl)propan-2-yl)-3-hydroxy-4H-pyran-4-one.

Some embodiments provided herein describe a compound, or a pharmaceutically acceptable salt thereof, having the structure of Formula (Ia):

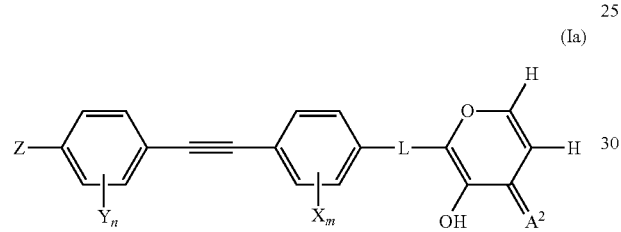

(Ia)

wherein, n is 0, 1, or 2;

m is 0, 1, or 2;

$A^2$ is O or S;

L is selected from *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

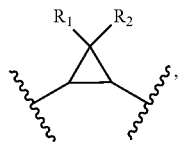

wherein the * denotes a bond to the 3-hydroxy-4H-pyran-4-one ring or 3-hydroxy-4H-pyran-4-thione ring;

$R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_1$-$C_4$ alkylene)-$N(R^{12})$-$SO2R^{11}$, optionally substituted ($C_1$-$C_4$ alkylene)-$SO2R^{11}$, or optionally substituted ($C_0$-$C_4$ alkylene)$N(R^{11})$—PO (optionally substituted $C_1$-$C_4$ alkyl)$_2$;

$R^2$, $R^4$, and $R^5$ are each independently H or optionally substituted $C_1$-$C_3$ alkyl;

X is halogen or optionally substituted $C_1$-$C_3$ alkyl;

Y is halogen or optionally substituted $C_1$-$C_3$ alkyl;

Z is H, -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$;

L2 is a bond, optionally substituted $C_1$-$C_4$ alkylene, —C(O)—, or —$SO_2$—;

G is optionally substituted heterocyclyl, optionally substituted heteroaryl, —$N(R^{13})_2$, —$OR^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently selected from H or optionally substituted alkyl;

each $R^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^H$ is independently selected from H or optionally substituted alkyl;

provided that if $R^1$ if H, then $R^3$ is not H; or if $R^3$ is H, then $R^1$ is not H.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In some embodiments, $R^1$ and $R^3$ are each independently H, optionally substituted ($C_1$-$C_4$ alkylene)-$OR^{11}$, optionally substituted ($C_1$-$C_4$ alkylene)-N($R^{11}$)$_2$, optionally substituted ($C_1$-$C_4$ alkylene)-N($R^{12}$)—$SO_2R^{11}$, or optionally substituted ($C_1$-$C_4$ alkylene)-$SO_2R^{11}$. In some embodiments, $R^1$ and $R^3$ are each independently H, ($C_1$-$C_4$ alkylene)-OH, ($C_1$-$C_4$ alkylene)-$NH_2$, ($C_1$-$C_4$ alkylene)-NH—$SO_2$Me, or ($C_1$-$C_4$ alkylene)-$SO_2$Me.

In some embodiments, $R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-N($R^{11}$)$_2$, optionally substituted ($C_1$-$C_4$ alkylene)N($R^{12}$)—$COR^{11}$, optionally substituted ($C_1$-$C_4$ alkylene)N($R^{12}$)—$CO_2R^{11}$, optionally substituted ($C_1$-$C_4$ alkylene)N($R^{12}$)—CON($R^{11}$)$_2$, optionally substituted ($C_1$-$C_4$ alkylene)N($R^{12}$)—$SO_2N(R^{11})_2$, optionally substituted ($C_1$-$C_4$ alkylene)-O—$SO_2N(R^{11})_2$, optionally substituted ($C_1$-$C_4$ alkylene)-N($R^{12}$)—$SO_2R^{11}$, optionally substituted ($C_1$-$C_4$ alkylene)-$SO_2R^{11}$, or optionally substituted ($C_1$-$C_4$ alkylene)N($R^{11}$)—PO (optionally substituted $C_1$-$C_4$ alkyl)$_2$. In other embodiments, $R^1$ is optionally substituted ($C_1$-$C_4$ alkylene)-$OR^{11}$, optionally substituted ($C_1$-$C_4$ alkylene)-N($R^{11}$)$_2$, optionally substituted ($C_1$-$C_4$ alkylene)-N($R^{12}$)—$SO_2R^{11}$, or optionally substituted ($C_1$-$C_4$ alkylene)-$SO_2R^{11}$. In some embodiments, $R^1$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2$Me, or optionally substituted ($C_1$-$C_4$ alkylene)-$SO_2$Me.

In some embodiments, $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-N($R^{11}$)$_2$, optionally substituted ($C_1$-$C_4$ alkylene)N($R^{12}$)—$COR^{11}$, optionally substituted ($C_1$-$C_4$ alkylene)N($R^{12}$)—$CO_2R^{11}$, optionally substituted ($C_1$-$C_4$ alkylene)N($R^{12}$)—CON($R^{11}$)$_2$, optionally substituted ($C_1$-$C_4$ alkylene)N($R^{12}$)—$SO_2N(R^{11})_2$, optionally substituted ($C_1$-$C_4$ alkylene)-O—$SO_2N(R^{11})_2$, optionally substituted ($C_1$-$C_4$ alkylene)-N($R^{12}$)—$SO_2R^{11}$, optionally substituted ($C_1$-$C_4$ alkylene)-$SO_2R^{11}$, or optionally substituted ($C_1$-$C_4$ alkylene)N($R^{11}$)—PO (optionally substituted $C_1$-$C_4$ alkyl)$_2$. In other embodiments, $R^3$ is optionally substituted ($C_1$-$C_4$ alkylene)-$OR^{11}$, optionally substituted ($C_1$-$C_4$ alkylene)-N($R^{11}$)$_2$, optionally substituted ($C_1$-$C_4$ alkylene)-N($R^{12}$)—$SO_2R^{11}$, or optionally substituted ($C_1$-$C_4$ alkylene)-$SO_2R^{11}$. In some embodiments, $R^3$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2$Me, or optionally substituted ($C_1$-$C_4$ alkylene)-$SO_2$Me.

In some embodiments, $R^2$, $R^4$, and $R^5$ are each independently H or optionally substituted $C_1$-$C_3$ alkyl. In some embodiments, $R^2$ is H. In some embodiments, $R^4$ is H. In some embodiments, $R^5$ is H. In some embodiments, $R^2$, $R^4$, and $R^5$ are H. In some embodiments, $R^1$ and $R^2$ are H. In some embodiments, $R^3$ and $R^4$ are H.

In some embodiments, n is 0. In some embodiments, m is 0. In some embodiments, m is 1 or 2. In some embodiments, m is 1. In some embodiments, m is 2. In some embodiments, n is 1 or 2. In some embodiments, n is 1. In some embodiments, n is 2. In some embodiments, X is halogen. In some embodiments, X is F. In some embodiments, Y is halogen. In some embodiments, Y is F.

In some embodiments, Z is -L2-G, optionally substituted ($C_1$-$C_4$ alkylene)-OCON($R^{13}$)$_2$, optionally substituted ($C_1$-$C_4$ alkylene)-N($R^{14}$)CON($R^{13}$)$_2$, or optionally substituted ($C_1$-$C_4$ alkylene)-$SO_2N(R^{13})_2$. In some embodiments, Z is H or -L2-G, wherein L2 is $C_1$-$C_4$ alkylene and G is optionally substituted heterocyclyl. In some embodiments, Z is H. In some embodiments, Z is L2-G, wherein L2 is $C_1$-$C_4$ alkylene and G is optionally substituted heterocyclyl.

In some embodiments, L is *—$CR^1R^2$—$CR^3R^4$—; *—$CR^1R^2$—N($R^5$)—; or *—C(O)—N($R^5$)—. In some embodiments, L is *—$CR^1R^2$—$CR^3R^4$— or *—$CR^1R^2$—N($R^5$)—. In some embodiments, L is *—$CR^1R^2$—$CR^3R^4$— or *—C(O)—N($R^5$)—. In some embodiments, L is *—$CR^1R^2$—$CR^3R^4$—. In some embodiments, L is *—$CR^1R^2$—N($R^5$)—. In some embodiments, L is *—C(O)—N($R^5$)—.

In some embodiments, $A^2$ is O. In some embodiments, $A^2$ is S.

In some embodiments, a compound of Formula (I) or (Ia), or a pharmaceutically acceptable salt thereof, has the structure of formula (Ib):

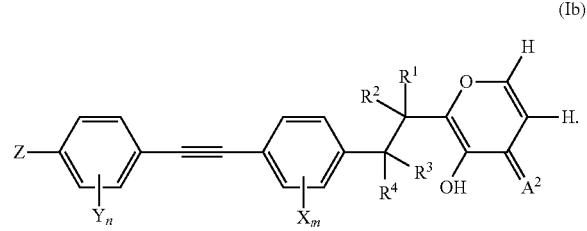

(Ib)

In some embodiments, a compound of Formula (I) or (Ia), or a pharmaceutically acceptable salt thereof, has the structure of formula (Ic):

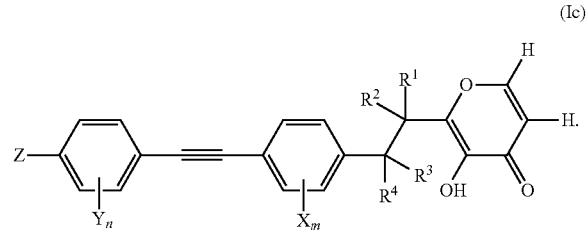

(Ic)

In some embodiments, a compound of Formula (I) or (Ia), or a pharmaceutically acceptable salt thereof, has the structure of formula (Id):

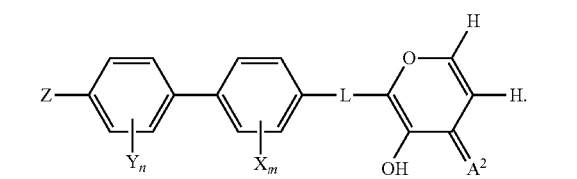

(Id)

Certain embodiments provided herein describe a compound, or a pharmaceutically acceptable salt thereof, of formula (Id):

wherein, n is 0, 1, or 2;

m is 0, 1, or 2;

$A^2$ is O or S;

L is selected from *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

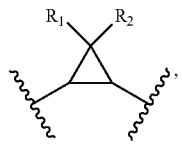

wherein the * denotes a bond to the 3-hydroxy-4H-pyran-4-one ring or 3-hydroxy-4H-pyran-4-thione ring;

$R^1$ and $R^3$ are each independently H, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_0$-$C_4$ alkylene)$N(R^{11})$—PO (optionally substituted $C_1$-$C_4$ alkyl)$_2$;

$R^2$, $R^4$, and $R^5$ are each independently H or optionally substituted $C_1$-$C_3$ alkyl;

X is halogen or optionally substituted $C_1$-$C_3$ alkyl;

Y is halogen or optionally substituted $C_1$-$C_3$ alkyl;

Z is H, -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$;

L2 is a bond, optionally substituted $C_1$-$C_4$ alkylene, —C(O)—, or —$SO_2$-;

G is optionally substituted heterocyclyl, optionally substituted heteroaryl, —$N(R^{13})_2$, —$OR^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently selected from H or optionally substituted alkyl;

each $R^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^{14}$ is independently selected from H or optionally substituted alkyl.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In some embodiments, $R^1$ and $R^3$ are each independently H, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^1$ and $R^3$ are each independently H, ($C_1$-$C_4$ alkylene)-OH, ($C_1$-$C_4$ alkylene)-$NH_2$, ($C_1$-$C_4$ alkylene)-NH—$SO_2$Me, or ($C_1$-$C_4$ alkylene)-$SO_2$Me.

In some embodiments, $R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In other embodiments, $R^1$ is optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^1$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2$Me, or optionally substituted ($C_1$-$C_4$ alkylene)-$SO_2$Me.

In some embodiments, $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR¹¹, —CON(R¹¹)₂, optionally substituted ($C_1$-$C_4$ alkylene)-CN, optionally substituted ($C_1$-$C_4$ alkylene)-OR¹¹, optionally substituted ($C_1$-$C_4$ alkylene)-N(R¹¹)₂, optionally substituted ($C_1$-$C_4$ alkylene)N(R¹²)—COR¹¹, optionally substituted ($C_1$-$C_4$ alkylene)N(R¹²)—CO₂R¹¹, optionally substituted ($C_1$-$C_4$ alkylene)N(R¹²)—CON(R¹¹)₂, optionally substituted ($C_1$-$C_4$ alkylene)N(R¹²)—SO₂N(R¹¹)₂, optionally substituted ($C_1$-$C_4$ alkylene)-O—SO₂N(R¹¹)₂, optionally substituted ($C_1$-$C_4$ alkylene)-N(R¹²)—SO₂R¹¹, optionally substituted ($C_1$-$C_4$ alkylene)-SO₂R¹¹, or optionally substituted ($C_1$-$C_4$ alkylene)N(R¹¹)—PO (optionally substituted $C_1$-$C_4$ alkyl)₂. In other embodiments, R³ is optionally substituted ($C_1$-$C_4$ alkylene)-OR¹¹, optionally substituted ($C_1$-$C_4$ alkylene)-N(R¹¹)₂, optionally substituted ($C_1$-$C_4$ alkylene)-N(R¹²)—SO₂R¹¹, or optionally substituted ($C_1$-$C_4$ alkylene)-SO₂R¹¹. In some embodiments, R³ is H, optionally substituted ($C_1$-$C_4$ alkylene)-OH, optionally substituted ($C_1$-$C_4$ alkylene)-NH₂, optionally substituted ($C_1$-$C_4$ alkylene)-NH—SO₂Me, or optionally substituted ($C_1$-$C_4$ alkylene)-SO₂Me.

In some embodiments, R², R⁴, and R⁵ are each independently H or optionally substituted $C_1$-$C_3$ alkyl. In some embodiments, R² is H. In some embodiments, R⁴ is H. In some embodiments, R⁵ is H. In some embodiments, R², R⁴, and R⁵ are H. In some embodiments, R¹ and R² are H. In some embodiments, R³ and R⁴ are H.

In some embodiments, n is 0. In some embodiments, m is 0. In some embodiments, m is 1 or 2. In some embodiments, m is 1. In some embodiments, m is 2. In some embodiments, n is 1 or 2. In some embodiments, n is 1. In some embodiments, n is 2. In some embodiments, X is halogen. In some embodiments, X is F. In some embodiments, Y is halogen. In some embodiments, Y is F.

In some embodiments, Z is -L2-G, optionally substituted ($C_1$-$C_4$ alkylene)-OCON(R¹³)₂, optionally substituted ($C_1$-$C_4$ alkylene)-N(R¹⁴)CON(R¹³)₂, or optionally substituted ($C_1$-$C_4$ alkylene)-SO₂N(R¹³)₂. In some embodiments, Z is H or -L2-G, wherein L2 is $C_1$-$C_4$ alkylene and G is optionally substituted heterocyclyl. In some embodiments, Z is H. In some embodiments, Z is L2-G, wherein L2 is $C_1$-$C_4$ alkylene and G is optionally substituted heterocyclyl.

In some embodiments, L is *—CR¹R²—CR³R⁴—; *—CR¹R²—N(R⁵)—; or *—C(O)—N(R⁵)—. In some embodiments, L is *—CR¹R²—CR³R⁴— or *—CR¹R²—N(R⁵)—. In some embodiments, L is *—CR¹R²—CR³R⁴— or *—C(O)—N(R⁵)—. In some embodiments, L is *—CR¹R²—CR³R⁴—. In some embodiments, L is *—CR¹R²—N(R⁵)—. In some embodiments, L is *—C(O)—N(R⁵)—.

In some embodiments, A² is O. In some embodiments, A² is S.

Other embodiments provided herein describe a compound, or a pharmaceutically acceptable salt thereof, having the structure of Formula (II):

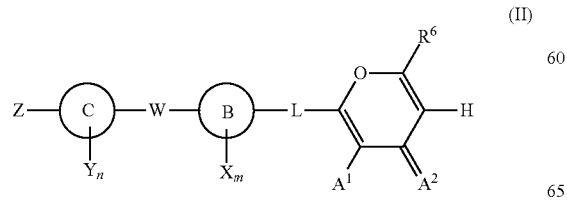

(II)

wherein,
n is 0, 1, or 2;
m is 0, 1, or 2;
A¹ is OH or SH;
A² is O or S;
L is selected from a bond, *—CR¹R²—CR³R⁴—; *—N(R⁵)—CR³R⁴—; *—CR¹R²—N(R⁵)—; *—O—CR³R⁴—; *—CR¹R²—O—; *—S—CR³R⁴—; *—CR¹R²—S—; *—N(R⁵)—C(O)—; *—C(O)—N(R⁵)—; *—N(R⁵)—S(O)₂—; *—S(O)₂—N(R⁵)—, or

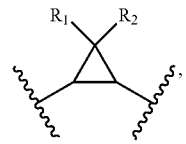

wherein the * denotes a bond to the 4H-pyran-4-one ring or 4H-pyran-4-thione ring;
R¹ and R³ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR¹¹, —CON(R¹¹)₂, optionally substituted ($C_0$-$C_4$ alkylene)-CN, optionally substituted ($C_0$-$C_4$ alkylene)-OR¹¹, optionally substituted ($C_0$-$C_4$ alkylene)-N(R¹¹)₂, optionally substituted ($C_0$-$C_4$ alkylene)N(R¹²)—COR¹¹, optionally substituted ($C_0$-$C_4$ alkylene)N(R¹²)—CO₂R¹¹, optionally substituted ($C_0$-$C_4$ alkylene)N(R¹²)—CON(R¹¹)₂, optionally substituted ($C_0$-$C_4$ alkylene)-SO₂N(R¹¹)₂, optionally substituted ($C_0$-$C_4$ alkylene)-SO₂R¹¹, optionally substituted ($C_0$-$C_4$ alkylene)N(R¹²)—SO₂N(R¹¹)₂, optionally substituted ($C_0$-$C_4$ alkylene)N(R¹²)—SO₂R¹¹, optionally substituted ($C_0$-$C_4$ alkylene)-O—SO₂N(R¹¹)₂, optionally substituted ($C_1$-$C_4$ alkylene)-N(R¹²)—SO₂R¹¹, optionally substituted ($C_1$-$C_4$ alkylene)-SO₂R¹¹, or optionally substituted ($C_0$-$C_4$ alkylene)N(R¹¹)—PO (optionally substituted $C_1$-$C_4$ alkyl)₂;
R², R⁴, and R⁵ are each independently H or optionally substituted $C_1$-$C_3$ alkyl;
R⁶ is H, halogen, optionally substituted alkyl, hydroxyl, alkoxyl, cyano, amino, or nitro;

is phenyl,

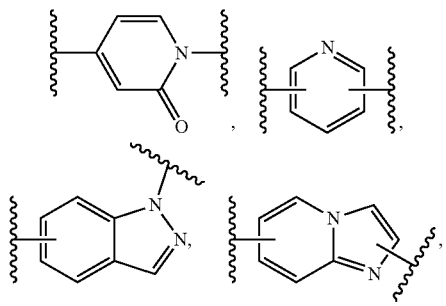

-continued

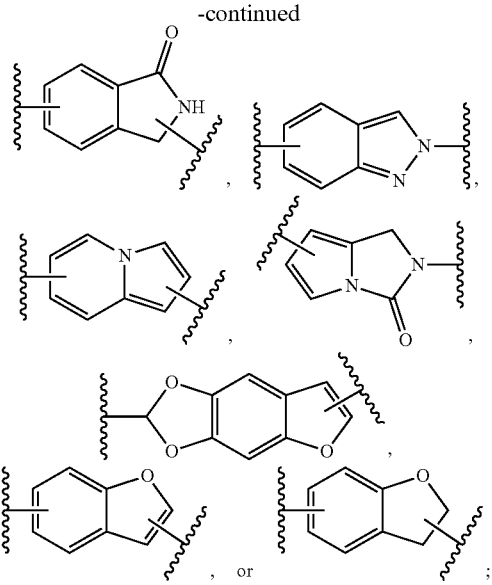

W is a bond, —C≡C—, —C≡C—C≡C—, —S—, —SO—, —SO$_2$—, —O—, —CR'R$^3$—, —C(=CR$^1$H)—, *—CR$^1$=CR$^3$—; *—CR$^1$R$^2$—CR$^3$R$^4$—; *—N(R$^5$)—CR$^3$R$^4$—; *—CR$^1$R$^2$—N(R$^5$)—; *—O—CR$^3$R$^4$—; *—CR$^1$R$^2$—O—; *—S—CR$^3$R$^4$—; *—CR$^1$R$^2$—S—; *—N(R$^5$)—C(O)—; *—C(O)—N(R$^5$)—; *—N(R$^5$)—S(O)$_2$—; *—S(O)$_2$—N(R$^5$)—, wherein the * denotes a bond to the ring having the Y groups;

Ⓒ is phenyl, cycloalkyl,

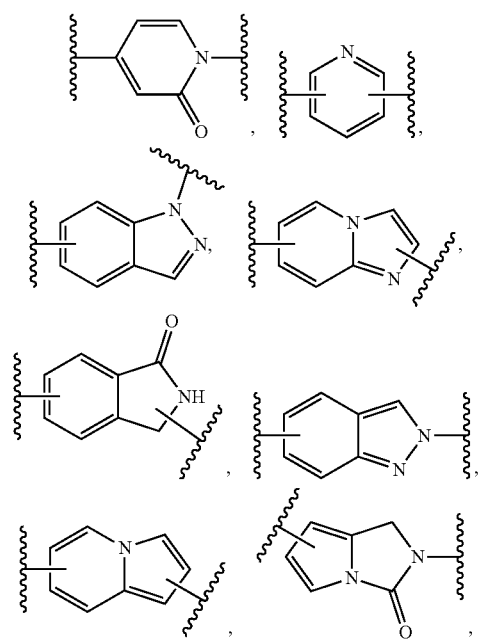

-continued

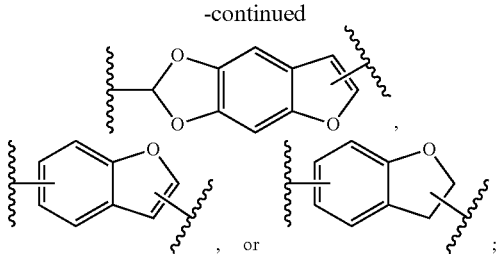

, or ;

provided that if

Ⓑ is phenyl, then

Ⓒ is not phenyl; and if

Ⓒ is phenyl, then

Ⓑ is not phenyl;

X is halogen or optionally substituted C$_1$-C$_3$ alkyl;
Y is halogen or optionally substituted C$_1$-C$_3$ alkyl;
Z is H, -L2-G, optionally substituted (C$_1$-C$_4$ alkylene)-OCON(R$^{13}$)$_2$, optionally substituted (C$_1$-C$_4$ alkylene)-N(R$^{14}$)CON(R$^{13}$)$_2$, or optionally substituted (C$_1$-C$_4$ alkylene)-SO$_2$N(R$^{13}$)$_2$;
L2 is a bond, optionally substituted C$_1$-C$_4$ alkylene, —C(O)—, or —SO$_2$-;
G is optionally substituted heterocyclyl, optionally substituted heteroaryl, —N(R$^{13}$)$_2$, —OR$^{13}$, halogen, or —CN;
each R$^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two R$^{11}$ groups together with the nitrogen to which they are attached join to form an optionally substituted N-heterocyclyl;
each R$^{12}$ is independently selected from H or optionally substituted alkyl;
each R$^{13}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^{14}$ is independently selected from H or optionally substituted alkyl.

In some embodiments, $R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In some embodiments, $R^1$ and $R^3$ are each independently H, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^1$ and $R^3$ are each independently H, ($C_1$-$C_4$ alkylene)-OH, ($C_1$-$C_4$ alkylene)-$NH_2$, ($C_1$-$C_4$ alkylene)-NH—$SO_2Me$, or ($C_1$-$C_4$ alkylene)-$SO_2Me$.

In some embodiments, $R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In other embodiments, $R^1$ is optionally substituted ($C_1$-$C_4$ alkylene)-$OR^{11}$, optionally substituted ($C_1$-$C_4$ alkylene)-N($R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$. In some embodiments, $R^1$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2Me$, or optionally substituted ($C_1$-$C_4$ alkylene)-$SO_2Me$.

In some embodiments, $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$. In other embodiments, $R^3$ is optionally substituted ($C_1$-$C_4$ alkylene)-$OR^{11}$, optionally substituted ($C_1$-$C_4$ alkylene)-N ($R^{11})_2$, optionally substituted ($C_1$-$C_4$ alkylene)-$N(R^{12})$—$SO_2R^{11}$, or optionally substituted ($C_1$-$C_4$ alkylene)-$SO_2R^{11}$.

In some embodiments, $R^3$ is H, optionally substituted ($C_1$-$C_4$ alkylene)-OH, optionally substituted ($C_1$-$C_4$ alkylene)-$NH_2$, optionally substituted ($C_1$-$C_4$ alkylene)-NH—$SO_2Me$, or optionally substituted ($C_1$-$C_4$ alkylene)-$SO_2Me$.

In some embodiments, $R^2$, $R^4$, and $R^5$ are each independently H or optionally substituted $C_1$-$C_3$ alkyl. In some embodiments, $R^2$ is H. In some embodiments, $R^4$ is H. In some embodiments, $R^5$ is H. In some embodiments, $R^2$, $R^4$, and $R^5$ are H. In some embodiments, $R^1$ and $R^2$ are H. In some embodiments, $R^3$ and $R^4$ are H.

In some embodiments, n is 0. In some embodiments, m is 0. In some embodiments, m is 1 or 2. In some embodiments, m is 1. In some embodiments, m is 2. In some embodiments, n is 1 or 2. In some embodiments, n is 1. In some embodiments, n is 2. In some embodiments, X is halogen. In some embodiments, X is F. In some embodiments, Y is halogen. In some embodiments, Y is F.

In some embodiments, Z is -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$. In some embodiments, Z is H or -L2-G, wherein L2 is $C_1$-$C_4$ alkylene and G is optionally substituted heterocyclyl. In some embodiments, Z is H. In some embodiments, Z is L2-G, wherein L2 is $C_1$-$C_4$ alkylene and G is optionally substituted heterocyclyl.

In some embodiments, W is a bond, or —C≡C—C≡C—. In other embodiments, W is a —C≡C— or —C≡C—C≡C—. In some embodiments, W is a bond.

In some embodiments, L is *—$CR^1R^2$—$CR^3R^4$—; *—$CR^1R^2$—$N(R^5)$—; or *—C(O)—$N(R^5)$—. In some embodiments, L is *—$CR^1R^2$—$CR^3R^4$— or *—$CR^1R^2$—$N(R^5)$—. In some embodiments, L is *—$CR^1R^2$—$CR^3R^4$— or *—C(O)—$N(R^5)$—. In some embodiments, L is *—$CR^1R^2$—$CR^3R^4$—. In some embodiments, L is *—$CR^1R^2$—$N(R^5)$—. In some embodiments, L is *—C(O)—$N(R^5)$—.

In some embodiments, $R^6$ is H, F, $C_1$, Br, alkyl, hydroxyl, alkoxyl, cyano, amino, or nitro. In some embodiments, $R^6$ is H.

In some embodiments, $A^1$ is OH and $A^2$ is O. In some embodiments, $A^1$ is SH and $A^2$ is O. In some embodiments, $A^1$ is SH and $A^2$ is S. In some embodiments, $A^1$ is OH and $A^2$ is S.

In some embodiments,  is phenyl,
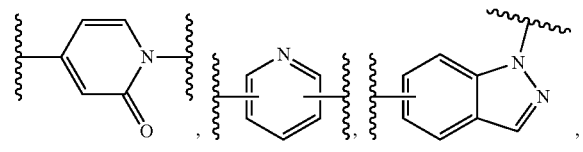,
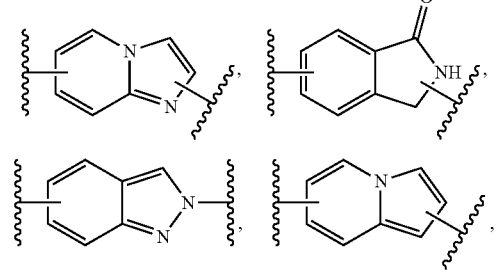,
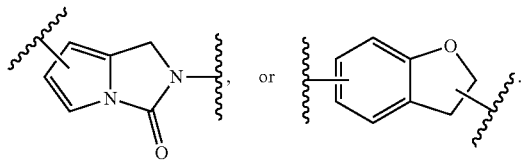.
In some embodiments,  is phenyl. In some embodiments,  is
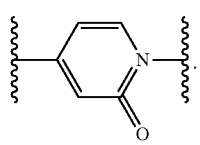.
In some embodiments,  is
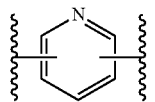.
In some embodiments, 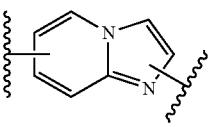 is
.
In some embodiments, 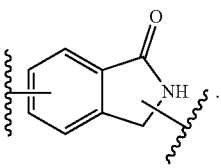
In some embodiments,  is
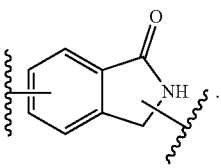.
In some embodiments, 

is
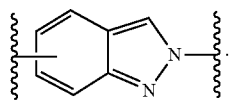
In some embodiments,
B
is
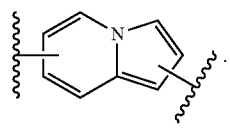
In some embodiments,
B
is
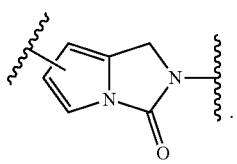
In some embodiments,
B
is
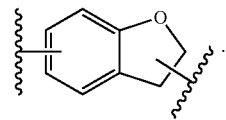
In some embodiments,
C
is phenyl, cycloalkyl,
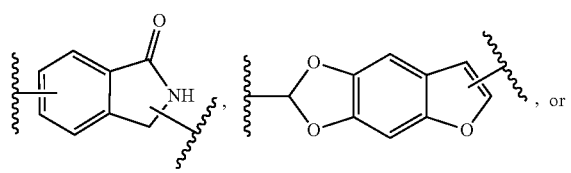, or
-continued
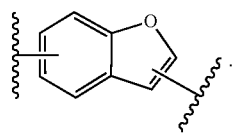
In some embodiments,
C
is phenyl. In some embodiments,
C
is cycloalkyl. In some embodiments,
C
is
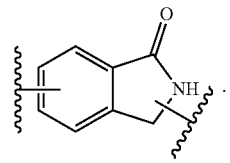
In some embodiments,
C
is
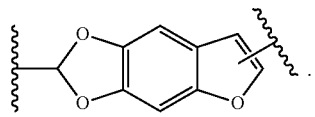
In some embodiments,
C is

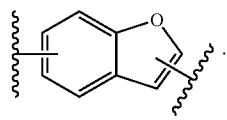

In some embodiments,

Ⓒ is phenyl or cycloalkyl. In some embodiments,

Ⓒ is phenyl or $C_3$-6 cycloalkyl. In some embodiments,

Ⓒ is phenyl or cyclopropyl.

In some embodiment, W is —C≡C— or —C≡C—CC—; and

Ⓒ is phenyl or cyclopropyl. In some embodiments,

Ⓑ is

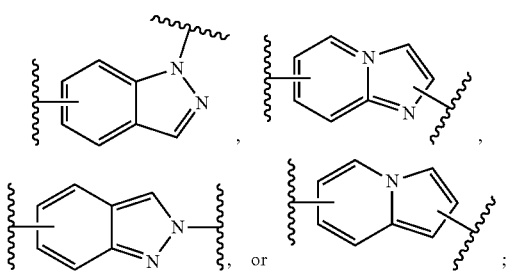

W is bond, —C≡C— or —C≡C—C≡C—; and

Ⓒ is phenyl or $C_3$-6 cycloalkyl. In some embodiments,

Ⓑ is

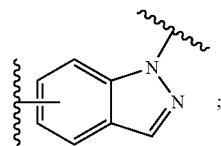

W is —C≡C—C≡C—; and

Ⓒ is cyclopropyl.

In some embodiments, a compound of Formula (II) is selected from:

2-(1-(4-(benzofuro[6,5-d][1,3]dioxol-6-yl)phenyl)-3-(2-fluoroethylamino)propan-2-yl)-3-hydroxy-4H-pyran-4-one;

2-(1-(4-(benzofuran-2-yl)phenylthio)-2-(2-fluoroethylamino)ethyl)-3-hydroxy-4H-pyran-4-one;

N-(2-fluoroethyl)-2-(3-hydroxy-4-oxo-4H-pyran-2-yl)-3-(6-(4-(2-hydroxyethyl)phenyl)-3-oxo-1H-pyrrolo[1,2-c]imidazol-2(3H)-yl)propanamide;

2-(1-(5-(cyclopropylethynyl)-2H-indazol-2-yl)-3-(2-fluoroethylamino)propan-2-yl)-3-hydroxy-4H-pyran-4-one;

2-(1-(6-(cyclopropylethynyl)imidazo[1,2-a]pyridin-2-yl)-3-(2-fluoroethylamino)propan-2-yl)-3-hydroxy-4H-pyran-4-one;

2-(1-(5-(cyclopropylbuta-1,3-diynyl)-1H-indazol-1-yl)-3-(2-fluoroethylamino)propan-2-yl)-3-hydroxy-4H-pyran-4-one;

5-(cyclopropylethynyl)-2-(3-(2-fluoroethylamino)-2-(3-hydroxy-4-oxo-4H-pyran-2-yl)propyl)isoindolin-1-one;

2-(1-(6-(cyclopropylethynyl)indolizin-2-yl)-3-(2-fluoroethylamino)propan-2-yl)-3-hydroxy-4H-pyran-4-one;

3-hydroxy-2-(6-(phenylethynyl)-2,3-dihydrobenzofuran-2-yl)-4H-pyran-4-one;

N-(2,2-difluoroethyl)-3-(4-((4-(1,2-dihydroxyethyl)phenyl)ethynyl)-2-oxopyridin-1(2H)-yl)-2-(3-hydroxy-4-oxo-4H-pyran-2-yl)propanamide; or 5-(6-(3-(2-fluoroethylamino)-2-(3-hydroxy-4-oxo-4H-pyran-2-yl)propyl)pyridin-3-yl)isoindolin-1-one.

In some embodiments, the heterocyclic LpxC inhibitory compound described in Formula (I), (Ia), (Ib), (Ic), (Id), or (II) are provided in Table 1.

TABLE 1

| Compound No. | Name | Structure | Mass [M + H] |
|---|---|---|---|
| 1 | 3-hydroxy-2-(1-(methylsulfonyl)-2-(4-((4-(morpholinomethyl)phenyl)-ethynyl)phenyl)ethyl)-4H-pyran-4-one | 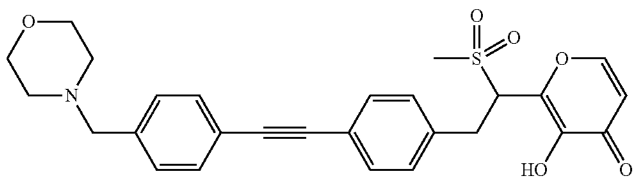 [SMILES: CS(=O)(=O)C(Cc1ccc(C#Cc2ccc(CN3CCOCC3)cc2)cc1)c1occc(=O)c1O] | 494.36 |
| 2 | 3-hydroxy-4-oxo-N-(4-(phenylbuta-1,3-diyn-1-yl)phenyl)-4H-pyran-2-carboxamide | 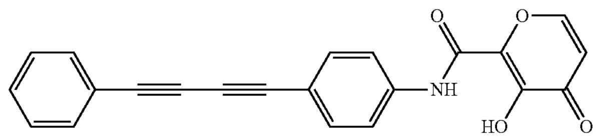 [SMILES: O=C(Nc1ccc(C#CC#Cc2ccccc2)cc1)c1occc(=O)c1O] | 356.02 |
| 3 | N-(3-([1,1'-biphenyl]-4-yl)-2-(3-hydroxy-4-oxo-4H-pyran-2-yl)propyl)methanesulfonamide | 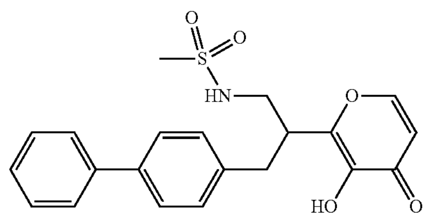 [SMILES: CS(=O)(=O)NCC(Cc1ccc(-c2ccccc2)cc1)c1occc(=O)c1O] | 400.22 |
| 4 | 2-(1-([1,1'-biphenyl]-4-yl)-3-(methylsulfonyl)propan-2-yl)-3-hydroxy-4H-pyran-4-one | 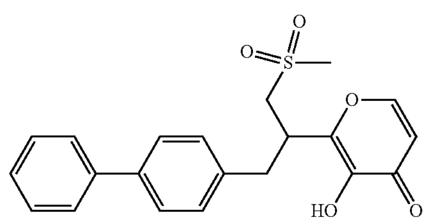 [SMILES: CS(=O)(=O)CC(Cc1ccc(-c2ccccc2)cc1)c1occc(=O)c1O] | 385.15 |
| 5 | 2-(1-([1,1'-biphenyl]-4-yl)-3-hydroxypropan-2-yl)-3-hydroxy-4H-pyran-4-one | 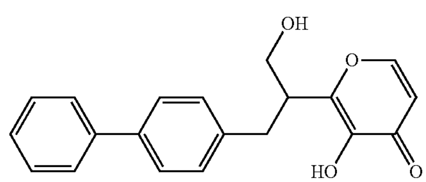 | 323.32 |
| 6 | 2-(1-([1,1'-biphenyl]-4-yl)-3-aminopropan-2-yl)-3-hydroxy-4H-pyran-4-one | 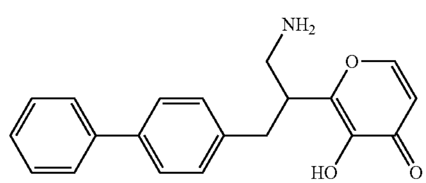 [SMILES: NCC(Cc1ccc(-c2ccccc2)cc1)c1occc(=O)c1O] | 322.34 |
| 7 | 2-((([1,1'-biphenyl]-4-yl(2-hydroxyethyl)amino)methyl)-3-hydroxy-4H-pyran-4-one | 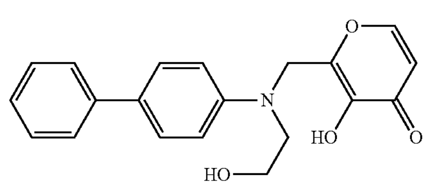 [SMILES: O=c1ccoc(CN(CCO)c2ccc(-c3ccccc3)cc2)c1O] | 338.18 |

In some embodiments, the heterocyclic LpxC inhibitory compound described in Formulas (I) and (II) is provided in Table 2.

TABLE 2

| Compound No. | Name | Structure |
|---|---|---|
| 8 | 2-(1-(2-fluoroethylamino)-3-(4-(4-(morpholinomethyl)phenethyl)phenyl)-propan-2-yl)-3-hydroxy-4H-pyran-4-one | 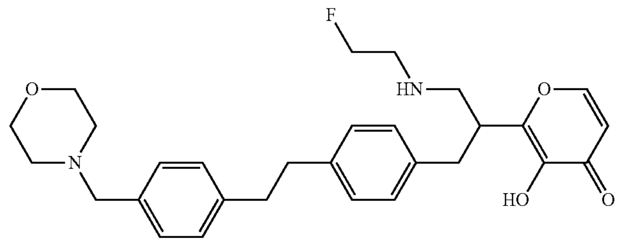 [SMILES: O=c1ccoc(C(CNCCF)Cc2ccc(CCc3ccc(CN4CCOCC4)cc3)cc2)c1O] |
| 9 | 2-(1-(2-fluoroethylamino)-3-(4-(4-(morpholinomethyl)phenylthio)phenyl)-propan-2-yl)-3-hydroxy-4H-pyran-4-one | 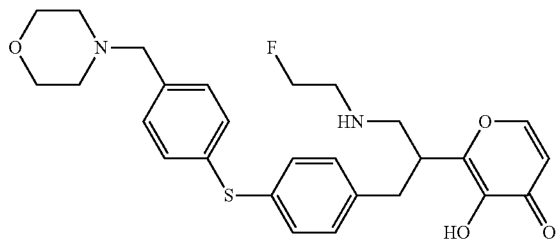 [SMILES: O=c1ccoc(C(CNCCF)Cc2ccc(Sc3ccc(CN4CCOCC4)cc3)cc2)c1O] |
| 10 | (E)-2-(1-(2-fluoroethylamino)-3-(4-(4-(morpholinomethyl)styryl)phenyl)-propan-2-yl)-3-hydroxy-4H-pyran-4-one | 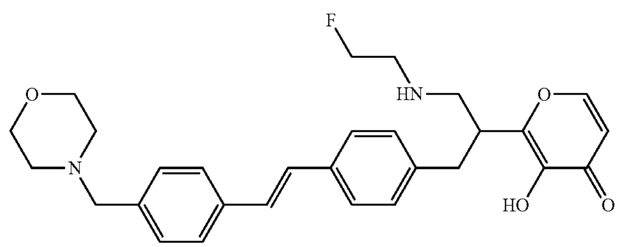 [SMILES: O=c1ccoc(C(CNCCF)Cc2ccc(/C=C/c3ccc(CN4CCOCC4)cc3)cc2)c1O] |
| 11 | 2-(1-(4-(benzofuro[6,5-d][1,3]dioxol-6-yl)phenyl)-3-(2-fluoroethylamino)propan-2-yl)-3-hydroxy-4H-pyran-4-one | 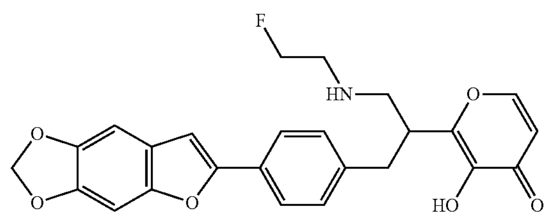 [SMILES: O=c1ccoc(C(CNCCF)Cc2ccc(-c3cc4cc5c(cc4o3)OCO5)cc2)c1O] |
| 12 | 2-(1-(4-(benzofuran-2-yl)phenylthio)-2-(2-fluoroethylamino)ethyl)-3-hydroxy-4H-pyran-4-one | 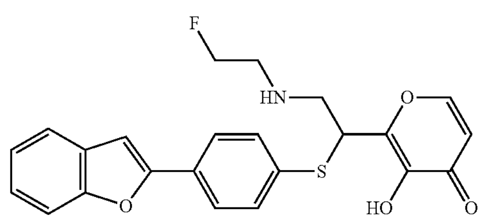 [SMILES: O=c1ccoc(C(CNCCF)Sc2ccc(-c3cc4ccccc4o3)cc2)c1O] |
| 13 | N-(2-fluoroethyl)-2-(3-hydroxy-4-oxo-4H-pyran-2-yl)-3-(6-(4-(2-hydroxyethyl)phenyl)-3-oxo-1H-pyrrolo[1,2-c]imidazol-2(3H)-yl)propenamide | 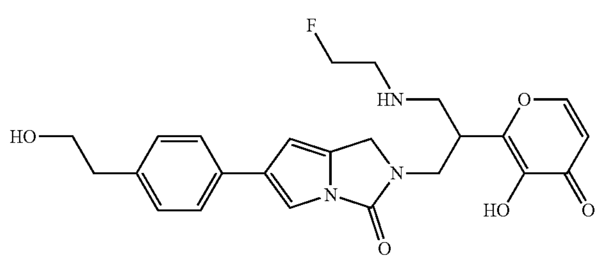 [SMILES: O=C1N(CC(CNCCF)c2occc(=O)c2O)Cc2cc(-c3ccc(CCO)cc3)cn21] |

TABLE 2-continued

| Compound No. | Name | Structure |
|---|---|---|
| 14 | 2-(1-(5-(cyclopropylethynyl)-2H-indazol-2-yl)-3-(2-fluoroethylamino)propan-2-yl)-3-hydroxy-4H-pyran-4-one | 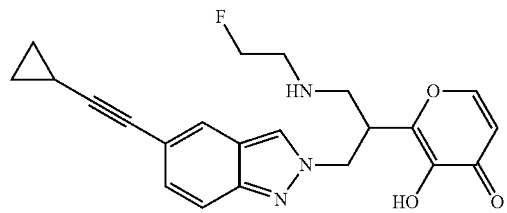 [SMILES: O=c1ccoc(C(CNCCF)Cn2cc3cc(C#CC4CC4)ccc3n2)c1O] |
| 15 | 2-(1-(6-(cyclopropylethynyl)imidazo[1,2-a]pyridin-2-yl)-3-(2-fluoroethylamino)propan-2-yl)-3-hydroxy-4H-pyran-4-one | 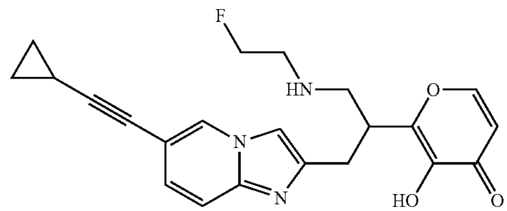 [SMILES: O=c1ccoc(C(CNCCF)Cc2cn3cc(C#CC4CC4)ccc3n2)c1O] |
| 16 | 2-(1-(5-(cyclopropylbuta-1,3-diynyl)-1H-indazol-1-yl)-3-(2-fluoroethylamino)propan-2-yl)-3-hydroxy-4H-pyran-4-one | 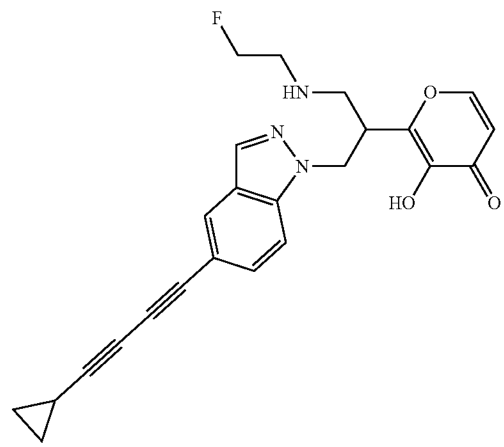 [SMILES: O=c1ccoc(C(CNCCF)Cn2ncc3cc(C#CC#CC4CC4)ccc32)c1O] |
| 17 | 5-(cyclopropylethynyl)-2-(3-(2-fluoroethylamino)-2-(3-hydroxy-4-oxo-4H-pyran-2-yl)propyl)isoindolin-1-one | 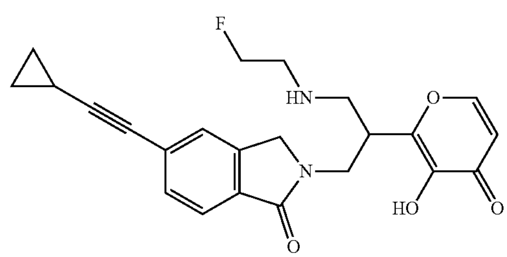 [SMILES: O=C1c2ccc(C#CC3CC3)cc2CN1CC(CNCCF)c1occc(=O)c1O] |
| 18 | 2-(1-(6-(cyclopropylethynyl)indolizin-2-yl)-3-(2-fluoroethylamino)propan-2-yl)-3-hydroxy-4H-pyran-4-one | 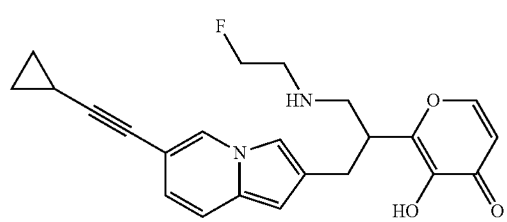 [SMILES: O=c1ccoc(C(CNCCF)Cc2cc3ccc(C#CC4CC4)cn3c2)c1O] |
| 19 | 3-hydroxy-2-(6-(phenylethynyl)-2,3-dihydrobenzofuran-2-yl)-4H-pyran-4-one | 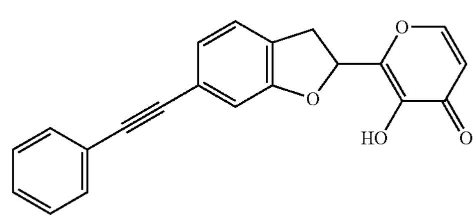 [SMILES: O=c1ccoc(C2Cc3ccc(C#Cc4ccccc4)cc3O2)c1O] |

TABLE 2-continued

| Compound No. | Name | Structure |
|---|---|---|
| 20 | N-(2,2-difluoroethyl)-3-(4-((4-(1,2-dihydroxyethyl)phenyl)ethynyl)-2-oxopyridin-1(2H)-yl)-2-(3-hydroxy-4-oxo-4H-pyran-2-yl)propanamide | 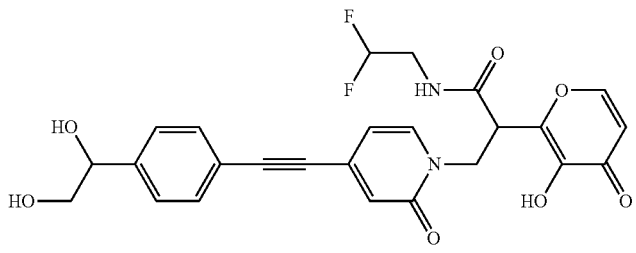 [SMILES: O=C(NCC(F)F)C(Cn1ccc(C#Cc2ccc(C(O)CO)cc2)cc1=O)c1occc(=O)c1O] |
| 21 | 5-(6-(3-(2-fluoroethylamino)-2-(3-hydroxy-4-oxo-4H-pyran-2-yl)propyl)pyridin-3-yl)isoindolin-1-one | 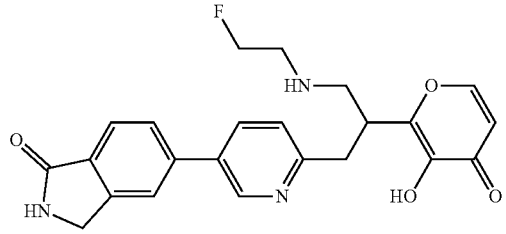 [SMILES: O=C1NCc2cc(-c3ccc(CC(CNCCF)c4occc(=O)c4O)nc3)ccc21] |

Preparation of Compounds

The compounds used in the chemical reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Alternatively, specific and analogous reactants can be identified through the indices of known chemicals and reactions prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the heterocyclic LpxC inhibitory compound described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heterocyclic LpxC inhibitory compound as described herein is administered as a pure chemical. In other embodiments, the heterocyclic LpxC inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, Pa. (2005)).

Provided herein is a pharmaceutical composition comprising at least one heterocyclic LpxC inhibitory compound, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound of Formula (I), (Ia), (Ib), (Ic), (Id), or (II), or a pharmaceutically acceptable salt thereof, and a pharmaceutically acceptable excipient.

In certain embodiments, the heterocyclic LpxC inhibitory compound as described by Formula (I), (Ia), (Ib), (Ic), (Id), or (II) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, $21^{st}$ Ed. Mack Pub. Co., Easton, Pa. (2005)).

The dose of the composition comprising at least one heterocyclic LpxC inhibitory compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

LpxC, Lipid A and Gram-Negative Bacteria

Metalloproteins influence a vast diversity of biological systems, biological processes, and diseases. For example, UDP-{3-O—[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of gram-negative bacteria. LpxC is a zinc(II)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of gram-negative bacteria, making LpxC an attractive target to treat gram-negative infections.

In recent years, there has been an increase in resistant and multi-drug resistant strains of bacteria. Thus, there is a need for new antibiotics, especially with new mechanisms of action. There remains a need for metalloprotein modulators of LpxC useful in the field of therapeutics, diagnostics, and research.

One embodiment provides a method of inhibiting UDP-{3-O—[(R)-3-hydroxymyristoyl]}-N-acetylglucosamine deacetylase enzyme comprising contacting the enzyme with a compound of Formula (I), (Ia), (Ib), (Ic), (Id), or (II).

Methods of Treatment

Disclosed herein is a method of inhibiting LpxC comprising contacting LpxC with a compound of Formula (I), (Ia), (Ib), (Ic), (Id), or (II). Disclosed herein are methods of treating disease wherein the inhibition of bacterial growth is indicated. Such disease includes gram-negative bacterial infection. In some embodiments, the method of treating a gram-negative bacterial infection in a patient in need thereof comprises administering to the patient a pharmaceutical composition comprising a compound of Formula (I), (Ia), (Ib), (Ic), (Id), or (II), or a pharmaceutically acceptable salt thereof, and a pharmaceutically acceptable excipient. In some embodiments, the gram-negative bacterial infection is selected from pneumonia, sepsis, cystic fibrosis, intra-abdominal infection, skin infections and urinary tract infection. In some embodiments, the gram-negative bacterial infection is a urinary tract infection (UTI), a hospital acquired/ventilator-associated pneumonia (HAP/VAP), or an intra-abdominal infection (IAD. In some embodiments, the gram-negative bacterial infection is selected from chronic urinary tract infections, complicated urinary tract infections, cystitis, pyelonephritis, urethritis, recurrent urinary tract infections, bladder infections, urethral infections, or kidney infections. In some embodiments, the compounds described herein are used for the treatment of chronic urinary tract infections. In some embodiments, the compounds described herein are used for the treatment of complicated urinary tract infections. In other embodiments, the compounds described herein are used for the treatment of complicated intra-abdominal infection. In some embodiments, the compounds described herein are used for the treatment of chronic intra-abdominal infection. In other embodiments, the compounds described herein are used for the treatment of hospital acquired pneumonia (HAP) or ventilator associated pneumonia (VAP). In some embodiments the administration is to treat an existing infection. In some embodiments the administration is provided as prophylaxis.

In some embodiments the heterocyclic LpxC inhibitory compound as described herein is used for treating conditions caused by the bacterial production of endotoxin and, in particular, by gram-negative bacteria and bacteria that use LpxC in the biosynthesis of lipopolysaccharide (LPS) or endotoxin. In some embodiments, the method of treating a condition caused by endotoxin or LPS in a patient in need thereof comprises administering to the patient a pharmaceutical composition comprising a compound of Formula (I), (Ia), (Ib), (Ic), (Id), or (II), or a pharmaceutically acceptable salt thereof, and a pharmaceutically acceptable excipient. In another embodiment, the heterocyclic LpxC inhibitory compounds as described herein are useful in the treatment of conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). In some embodiments, the method of treating a condition caused by endotoxin or LPS in a patient in need thereof comprises administering to the patient a pharmaceutical composition comprising a compound of Formula (I), (Ia), (Ib), (Ic), (Id), or (II), or a pharmaceutically acceptable salt thereof, and a pharmaceutically acceptable excipient, wherein the condition caused by endotoxin or LPS is selected from sepsis, septic shock, systemic inflammation, localized inflammation, chronic obstructive pulmonary disease (COPD) and acute exacerbations of chronic bronchitis (AECB).

In other embodiments, the compounds of the disclosure can be used for the treatment of a serious or chronic respiratory tract infection or complicated urinary tract infections including serious lung and nosocomial infections such as those caused by *Enterobacter aerogenes*, *Enterobacter cloacae*, *Escherichia coli*, *Klebsiella pneumoniae*, *Klebsiella oxytoca*, *Proteus mirabilis*, *Serratia marcescens*, *Stenotrophomonas maltophilia*, *Pseudomonas aeruginosa*, *Burkholderia cepacia*, *Acinetobacter baumannii*, *Alcaligenes xylosoxidans*, *Flavobacterium meningosepticum*, *Providencia sluarlii* and *Citrobacter freundi*, *Haemophilus influenzae*, *Legionella species*, *Moraxella catarrhalis*, *Enterobacter* species, *Acinetobacter* species, *Klebsiella* species, *Burkholderia* species and *Proteus* species, and infections caused by other bacterial species such as *Neisseria* species, *Shigella* species, *Salmonella* species, *Helicobacter pylori*, Vibrionaceae and *Bordetella* species as well as the infections caused by a *Brucella* species, *Francisella tularensis* and/or *Yersinia pestis*.

Other embodiments and uses will be apparent to one skilled in the art in light of the present disclosures. The following examples are provided merely as illustrative of various embodiments and shall not be construed to limit the invention in any way.

EXAMPLES

I. Biological Evaluation

Example 1: In Vitro Assays to Screen Compounds and Metalloprotein Modulators

Bacterial Susceptibility Testing

Minimal inhibitory concentrations (MIC) were determined by the broth microdilution method in accordance with the Clinical and Laboratory Standards Institute (CLSI) guidelines. In brief, organism suspensions were adjusted to a 0.5 McFarland standard to yield a final inoculum between $3 \times 10^5$ and $7 \times 10^5$ colony-forming units (CFU)/mL. Drug dilutions and inocula were made in sterile, cation adjusted Mueller-Hinton Broth (Beckton Dickinson). An inoculum volume of 100 µL was added to wells containing 100 µL of broth with 2-fold serial dilutions of drug. All inoculated microdilution trays were incubated in ambient air at 35° C. for 18-24 h. Following incubation, the lowest concentration of the drug that prevented visible growth (OD600 nm<0.05) was recorded as the MIC. Performance of the assay was monitored by the use of laboratory quality-control strains and levofloxacin, a compound with a defined MIC spectrum, in accordance with CLSI guidelines.

Table 3. Exemplary in vitro assay data against select bacteria for compounds in embodiments of the disclosure.

TABLE 3

| Compound No. | E. coli MIC | S. aureus MIC |
|---|---|---|
| 1 | D | |
| 2 | D | |
| 3 | D | D |
| 4 | D | D |
| 5 | D | D |
| 6 | C | C |
| 7 | D | D |

Note:
Microbiological activity data are designated within the following ranges:
A: ≤1 µg/mL
B: >1 µg/mL to ≤8.0 µg/mL
C: >8.0 µg/mL to ≤8.0 µg/mL
D: >32 µg/mL II. Preparation of Pharmaceutical Dosage Forms Example 1: Oral Capsule The active ingredient is a compound of Formula (I), or a pharmaceutically acceptable salt thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

We claim:
1. A compound, or a pharmaceutically acceptable salt thereof, having the structure of Formula (I):

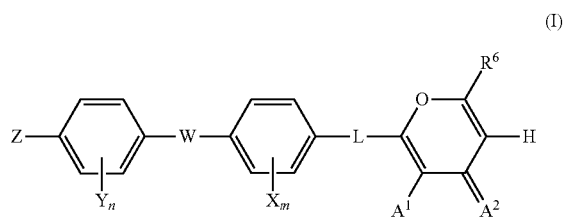

wherein,
n is 0, 1, or 2;
m is 0, 1, or 2;
$A^1$ is OH or SH;
$A^2$ is O or S;
L is *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

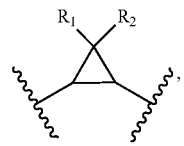

wherein the * denotes a bond to the 4H-pyran-4-one ring or 4H-pyran-4-thione ring;

$R^1$, $R^3$, and $R^5$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—$CON(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_0$-$C_4$ alkylene)$N(R^{11})$—PO (optionally substituted $C_1$-$C_4$ alkyl)$_2$;

$R^2$ and $R^4$ are each independently H or optionally substituted $C_1$-$C_3$ alkyl;

$R^6$ is H;

X is halogen or optionally substituted $C_1$-$C_3$ alkyl;

Y is halogen or optionally substituted $C_1$-$C_3$ alkyl;

W is a bond, —C≡C—, or —C≡C—C≡C—;

Z is H, -L2-G, optionally substituted ($C_1$-$C_4$ alkylene)-$OCON(R^{13})_2$, optionally substituted ($C_1$-$C_4$ alkylene)-$N(R^{14})CON(R^{13})_2$, or optionally substituted ($C_1$-$C_4$ alkylene)-$SO_2N(R^{13})_2$;

L2 is a bond, optionally substituted $C_1$-$C_4$ alkylene, —C(O)—, or —$SO_2$—;

G is optionally substituted heterocyclyl, optionally substituted heteroaryl, —$N(R^{13})_2$, —$OR^{13}$, or —CN;

each $R^{11}$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently H or optionally substituted alkyl;

each $R^{13}$ is independently H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and each $R^{14}$ is independently H or optionally substituted alkyl;

provided that if $R^1$ is H, then $R^3$ or $R^5$ is not H; or if $R^3$ is H, then $R^1$ or $R^5$ is not H; and if W is a bond, then $R^1$ is not propyl, —$CH_2CH_2OH$, —$CH_2CH(OH)CH_2OH$;

wherein:

$R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$; or $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$.

2. The compound of claim 1, or a pharmaceutically acceptable salt thereof, wherein:

$R^1$ is H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_1$-$C_4$ alkylene)$N(R^{11})$—PO (optionally substituted $C_1$-$C_4$ alkyl)$_2$; and $R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —$COR^{11}$, —$CON(R^{11})_2$, optionally substituted ($C_1$-$C_4$ alkylene)-CN, optionally substituted ($C_1$-$C_4$ alkylene)-$OR^{11}$, optionally substituted ($C_1$-$C_4$ alkylene)-$N(R^{11})_2$, optionally substituted ($C_1$-$C_4$ alkylene)$N(R^{12})$—$COR^{11}$, optionally substituted ($C_1$-$C_4$ alkylene)$N(R^{12})$—$CO_2R^{11}$, optionally substituted ($C_1$-$C_4$ alkylene)$N(R^{12})$—$CON(R^{11})_2$, optionally substituted ($C_1$-$C_4$ alkylene)$N(R^{12})$—$SO_2N(R^{11})_2$, optionally substituted ($C_1$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-

SO₂R¹¹, or optionally substituted (C₁-C₄ alkylene)N(R¹¹)—PO (optionally substituted C₁-C₄ alkyl)₂.

3. The compound of claim 1, or a pharmaceutically acceptable salt thereof, wherein:
R¹ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR¹¹, —CON(R¹¹)₂, optionally substituted (C₁-C₄ alkylene)-CN, optionally substituted (C₁-C₄ alkylene)-OR¹¹, optionally substituted (C₁-C₄ alkylene)-N(R¹¹)₂, optionally substituted (C₁-C₄ alkylene)N(R¹²)—COR¹¹, optionally substituted (C₁-C₄ alkylene)N(R¹²)—CO₂R¹¹, optionally substituted (C₁-C₄ alkylene)N(R¹²)—CON(R¹¹)₂, optionally substituted (C₁-C₄ alkylene)N(R¹²)—SO₂N(R¹¹)₂, optionally substituted (C₁-C₄ alkylene)-O—SO₂N(R¹¹)₂, optionally substituted (C₁-C₄ alkylene)-N(R¹²)—SO₂R¹¹, optionally substituted (C₁-C₄ alkylene)-SO₂R¹¹, or optionally substituted (C₁-C₄ alkylene)N(R¹¹)—PO (optionally substituted C₁-C₄ alkyl)₂; and
R³ is H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR¹¹, —CON(R¹¹)₂, optionally substituted (C₁-C₄ alkylene)-CN, optionally substituted (C₁-C₄ alkylene)-OR¹¹, optionally substituted (C₁-C₄ alkylene)-N(R¹¹)₂, optionally substituted (C₁-C₄ alkylene)N(R¹²)—COR¹¹, optionally substituted (C₁-C₄ alkylene)N(R¹²)—CO₂R¹¹, optionally substituted (C₁-C₄ alkylene)N(R¹²)—CON(R¹¹)₂, optionally substituted (C₁-C₄ alkylene)N(R¹²)—SO₂N(R¹¹)₂, optionally substituted (C₁-C₄ alkylene)-O—SO₂N(R¹¹)₂, optionally substituted (C₁-C₄ alkylene)-N(R¹²)—SO₂R¹¹, optionally substituted (C₁-C₄ alkylene)-SO₂R¹¹, or optionally substituted (C₁-C₄ alkylene)N(R¹¹)—PO (optionally substituted C₁-C₄ alkyl)₂.

4. The compound of claim 1, or a pharmaceutically acceptable salt thereof, wherein R² and R⁴ are each independently H or optionally substituted C₁-C₃ alkyl; and R⁵ is H or unsubstituted alkyl.

5. The compound of claim 1, or a pharmaceutically acceptable salt thereof, wherein n is 0; and m is 0.

6. The compound of claim 1, or a pharmaceutically acceptable salt thereof, wherein Z is -L2-G, optionally substituted (C₁-C₄ alkylene)-OCON(R¹³)₂, optionally substituted (C₁-C₄ alkylene)-N(R¹⁴)CON(R¹³)₂, or optionally substituted (C₁-C₄ alkylene)-SO₂N(R¹³)₂.

7. The compound of claim 1, or a pharmaceutically acceptable salt thereof, wherein L is selected from *—CR¹R²—CR³R⁴—; *—CR¹R²—N(R⁵)—; or *—C(O)—N(R⁵)—.

8. The compound of claim 1, or a pharmaceutically acceptable salt thereof, wherein A¹ is OH; and A² is O.

9. The compound of claim 1, or a pharmaceutically acceptable salt thereof, wherein the compound is selected from:
3-hydroxy-2-(1-(methylsulfonyl)-2-(44(4-(morpholinomethyl)phenyl)ethynyl)phenyl)ethyl)-4H-pyran-4-one;
3-hydroxy-4-oxo-N-(4-(phenylbuta-1,3-diyn-1-yl)phenyl)-4H-pyran-2-carboxamide;
N-(3-([1,1'-biphenyl]-4-yl)-2-(3-hydroxy-4-oxo-4H-pyran-2-yl)propyl)methanesulfonamide;
2-(1-([1,1'-biphenyl]-4-yl)-3-(methylsulfonyl)propan-2-yl)-3-hydroxy-4H-pyran-4-one;
2-(1-([1,1'-biphenyl]-4-yl)-3-hydroxypropan-2-yl)-3-hydroxy-4H-pyran-4-one;
2-(1-([1,1'-biphenyl]-4-yl)-3-aminopropan-2-yl)-3-hydroxy-4H-pyran-4-one; and
2-(([1,1'-biphenyl]-4-yl(2-hydroxyethyl)amino)methyl)-3-hydroxy-4H-pyran-4-one.

10. The compound of claim 1, or a pharmaceutically acceptable salt thereof, having the structure of Formula (Ia), Formula (Ib), or Formula (Ic):

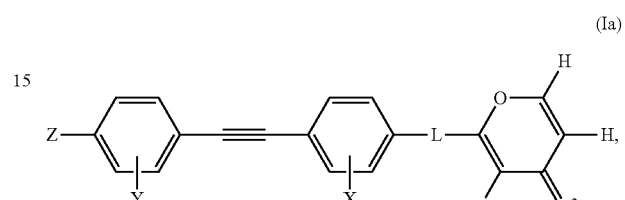

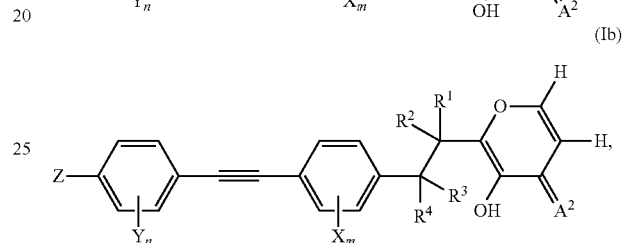

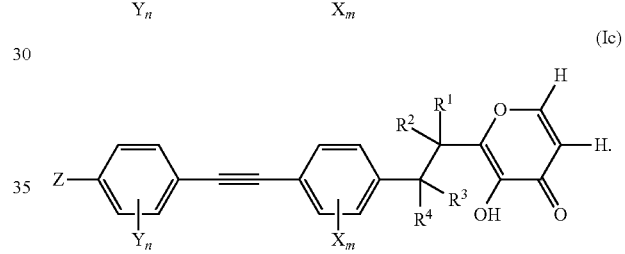

11. The compound of claim 1, wherein the compound, or a pharmaceutically acceptable salt thereof, has the structure of formula (Id):

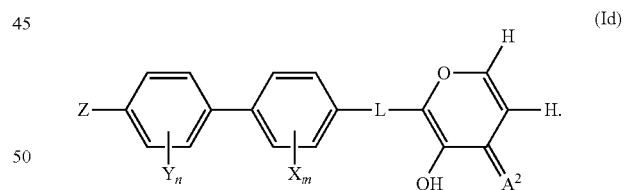

12. A compound, or a pharmaceutically acceptable salt thereof, having the structure of Formula (II):

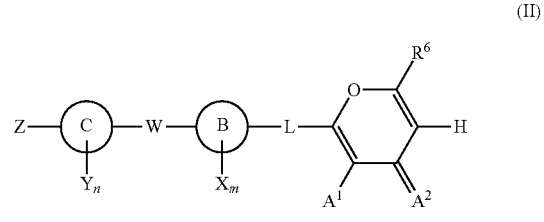

wherein, n is 0, 1, or 2;

m is 0, 1, or 2;

$A^1$ is OH;

$A^2$ is O;

L is a bond, *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; *—$S(O)_2$—$N(R^5)$—, or

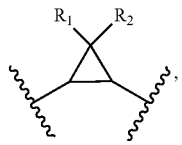

wherein the * denotes a bond to the 4H-pyran-4-one ring;

$R^1$ and $R^3$ are each independently H, unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —CON$(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)$N(R^{12})$—$COR^{11}$, optionally substituted ($C_0$-$C_4$ alkylene)$N(R^{12})$—$CO_2R^{11}$, optionally substituted ($C_0$-$C_4$ alkylene)$N(R^{12})$—CON$(R^{11})_2$, optionally substituted ($C_0$-$C_4$ alkylene)-$SO_2N(R^{11})_2$, optionally substituted ($C_0$-$C_4$ alkylene)-$SO_2R^{11}$, optionally substituted ($C_0$-$C_4$ alkylene)$N(R^{12})$—$SO_2N(R^{11})_2$, optionally substituted ($C_0$-$C_4$ alkylene)$N(R^{12})$—$SO_2R^{11}$, optionally substituted ($C_0$-$C_4$ alkylene)-O—$SO_2N(R^{11})_2$, optionally substituted ($C_1$-$C_4$ alkylene)-$N(R^{12})$—$SO_2R^{11}$, optionally substituted ($C_1$-$C_4$ alkylene)-$SO_2R^{11}$, or optionally substituted ($C_0$-$C_4$ alkylene)$N(R^{11})$—PO (optionally substituted $C_1$-$C_4$ alkyl)$_2$;

$R^2$, $R^4$, and $R^5$ are each independently H or optionally substituted $C_1$-$C_3$ alkyl;

$R^6$ is H;

Ⓑ is phenyl,

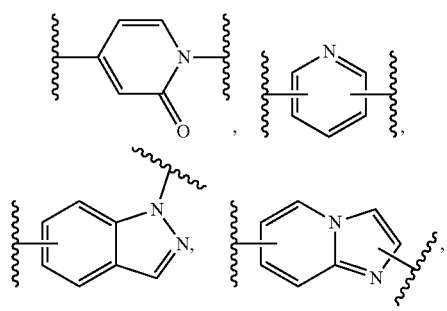

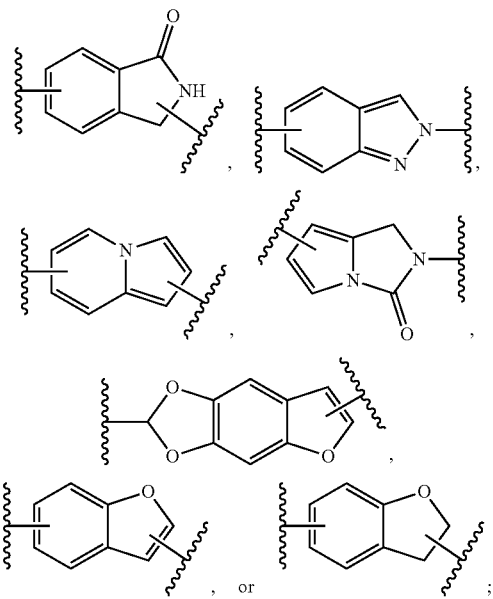

W is a bond, —S—, —SO—, —$SO_2$—, —O—, —$CR^1R^3$—, —C(=$CR^1H$)—, *—$CR^1$=$CR^3$—; *—$CR^1R^2$—$CR^3R^4$—; *—$N(R^5)$—$CR^3R^4$—; *—$CR^1R^2$—$N(R^5)$—; *—O—$CR^3R^4$—; *—$CR^1R^2$—O—; *—S—$CR^3R^4$—; *—$CR^1R^2$—S—; *—$N(R^5)$—C(O)—; *—C(O)—$N(R^5)$—; *—$N(R^5)$—$S(O)_2$—; or *—$S(O)_2$—$N(R^5)$—, wherein the * denotes a bond to

Ⓒ;

Ⓒ is phenyl, cycloalkyl,

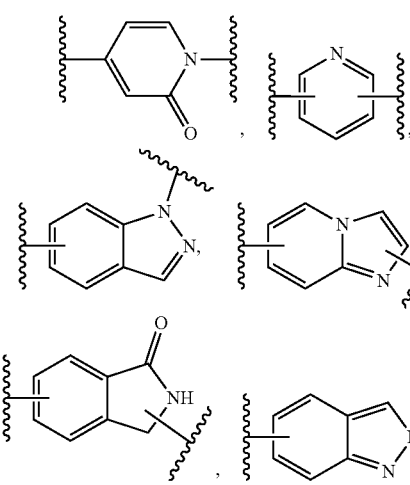

-continued

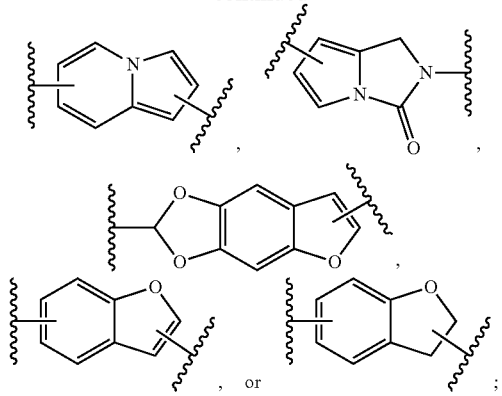

provided that if

Ⓑ is phenyl, then

Ⓒ is not phenyl; and
if

Ⓒ is phenyl, then

Ⓑ is not phenyl;
X is halogen or optionally substituted $C_1$-$C_3$ alkyl;
Y is halogen or optionally substituted $C_1$-$C_3$ alkyl;
Z is H, -L2-G, optionally substituted ($C_1$-$C_4$ alkylene)-OCON($R^{13}$)$_2$, optionally substituted ($C_1$-$C_4$ alkylene)-N($R^{14}$)CON($R^{13}$)$_2$, or optionally substituted ($C_1$-$C_4$ alkylene)-SO$_2$N($R^{13}$)$_2$;
L2 is a bond, optionally substituted $C_1$-$C_4$ alkylene, —C(O)—, or —SO$_2$—;
G is optionally substituted heterocyclyl, optionally substituted heteroaryl, —N($R^{13}$)$_2$, —OR$^{13}$, halogen, or —CN;
each $R^{11}$ is independently H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^{12}$ is independently H or optionally substituted alkyl;
each $R^{13}$ is independently H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{13}$ groups together with the nitrogen to which they are attached join to form an optionally substituted N-heterocyclyl; and
each $R^{14}$ is independently selected from H or optionally substituted alkyl.

13. The compound of claim 12, or a pharmaceutically acceptable salt thereof, wherein:
L is selected from *—CR$^1$R$^2$—CR$^3$R$^4$—; *—CR$^1$R$^2$—N(R$^5$)—; or *—C(O)—N(R$^5$)—;
$R^1$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR$^{11}$, —CON(R$^{11}$)$_2$, optionally substituted ($C_1$-$C_4$ alkylene)-CN, optionally substituted ($C_1$-$C_4$ alkylene)-OR$^{11}$, optionally substituted ($C_1$-$C_4$ alkylene)-N(R$^{11}$)$_2$, optionally substituted ($C_1$-$C_4$ alkylene)N(R$^{12}$)—COR$^{11}$, optionally substituted ($C_1$-$C_4$ alkylene)N(R$^{12}$)—CO$_2$R$^{11}$, optionally substituted ($C_1$-$C_4$ alkylene)N(R$^{12}$)—CON(R$^{11}$)$_2$, optionally substituted ($C_1$-$C_4$ alkylene)N(R$^{12}$)—SO$_2$N(R$^{11}$)$_2$, optionally substituted ($C_1$-$C_4$ alkylene)-O—SO$_2$N(R$^{11}$)$_2$, optionally substituted ($C_1$-$C_4$ alkylene)-N(R$^{12}$)—SO$_2$R$^{11}$, optionally substituted ($C_1$-$C_4$ alkylene)-SO$_2$R$^{11}$, or optionally substituted ($C_1$-$C_4$ alkylene)N(R$^{11}$)—PO (optionally substituted $C_1$-$C_4$ alkyl)$_2$;
$R^3$ is unsubstituted alkyl, optionally substituted aryl, optionally substituted aralkyl, optionally substituted heteroaryl, optionally substituted heteroaralkyl, optionally substituted heterocyclyl, optionally substituted heterocyclalkyl, —COR$^{11}$, —CON(R$^{11}$)$_2$, optionally substituted ($C_1$-$C_4$ alkylene)-CN, optionally substituted ($C_1$-$C_4$ alkylene)-OR$^{11}$, optionally substituted ($C_1$-$C_4$ alkylene)-N(R$^{11}$)$_2$, optionally substituted ($C_1$-$C_4$ alkylene)N(R$^{12}$)—COR$^{11}$, optionally substituted ($C_1$-$C_4$ alkylene)N(R$^{12}$)—CO$_2$R$^{11}$, optionally substituted ($C_1$-$C_4$ alkylene)N(R$^{12}$)—CON(R$^{11}$)$_2$, optionally substituted ($C_1$-$C_4$ alkylene)N(R$^{12}$)—SO$_2$N(R$^{11}$)$_2$, optionally substituted ($C_1$-$C_4$ alkylene)-O—SO$_2$N(R$^{11}$)$_2$, optionally substituted ($C_1$-$C_4$ alkylene)-N(R$^{12}$)—SO$_2$R$^{11}$, optionally substituted ($C_1$-$C_4$ alkylene)-SO$_2$R$^{11}$, or optionally substituted ($C_1$-$C_4$ alkylene)N(R$^{11}$)—PO (optionally substituted $C_1$-$C_4$ alkyl)$_2$; and
$R^2$, $R^4$, and $R^5$ are each independently H or optionally substituted $C_1$-$C_3$ alkyl;
n is 0; and
m is 0.

14. The compound of claim 12, or a pharmaceutically acceptable salt thereof, wherein Z is -L2-G, optionally substituted ($C_1$-$C_4$ alkylene)-OCON(R$^{13}$)$_2$, optionally substituted ($C_1$-$C_4$ alkylene)-N(R$^{14}$)CON(R$^{13}$)$_2$, or optionally substituted ($C_1$-$C_4$ alkylene)-SO$_2$N(R$^{13}$)$_2$.

15. The compound of claim 12, or a pharmaceutically acceptable salt thereof, wherein:

Ⓑ is phenyl,

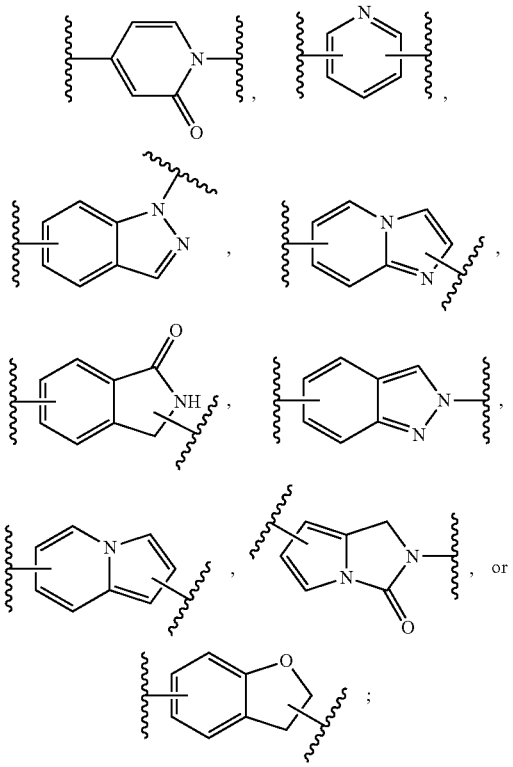

is phenyl, cycloalkyl,

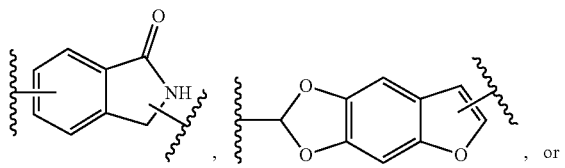

and

W is —C≡C— or —C≡C—C≡C—.

16. The compound of claim 12, or a pharmaceutically acceptable salt thereof, wherein the compound is selected from:
2-(1-(4-(benzofuro[6,5-d][1,3]dioxol-6-yl)phenyl)-3-(2-fluoroethylamino)propan-2-yl)-3-hydroxy-4H-pyran-4-one;
2-(1-(4-(benzofuran-2-yl)phenylthio)-2-(2-fluoroethylamino)ethyl)-3-hydroxy-4H-pyran-4-one;
N-(2-fluoroethyl)-2-(3-hydroxy-4-oxo-4H-pyran-2-yl)-3-(6-(4-(2-hydroxyethyl)phenyl)-3-oxo-1H-pyrrolo[1,2-c]imidazol-2(3H)-yl)propanamide;
2-(1-(5-(cyclopropylethynyl)-2H-indazol-2-yl)-3-(2-fluoroethylamino)propan-2-yl)-3-hydroxy-4H-pyran-4-one;
2-(1-(6-(cyclopropylethynyl)imidazo[1,2-a]pyridin-2-yl)-3-(2-fluoroethylamino)propan-2-yl)-3-hydroxy-4H-pyran-4-one;
2-(1-(5-(cyclopropylbuta-1,3-diynyl)-1H-indazol-1-yl)-3-(2-fluoroethylamino)propan-2-yl)-3-hydroxy-4H-pyran-4-one;
5-(cyclopropylethynyl)-2-(3-(2-fluoroethylamino)-2-(3-hydroxy-4-oxo-4H-pyran-2-yl)propyl)isoindolin-1-one;
2-(1-(6-(cyclopropylethynyl)indolizin-2-yl)-3-(2-fluoroethylamino)propan-2-yl)-3-hydroxy-4H-pyran-4-one;
3-hydroxy-2-(6-(phenylethynyl)-2,3-dihydrobenzofuran-2-yl)-4H-pyran-4-one;
N-(2,2-difluoroethyl)-3-(4-((4-(1,2-dihydroxyethyl)phenyl)ethynyl)-2-oxopyridin-1(2H)-yl)-2-(3-hydroxy-4-oxo-4H-pyran-2-yl)propanamide; and
5-(6-(3-(2-fluoroethylamino)-2-(3-hydroxy-4-oxo-4H-pyran-2-yl)propyl)pyridin-3-yl)isoindolin-1-one.

17. A pharmaceutical composition comprising a compound of claim 1, or a pharmaceutically acceptable salt thereof, and a pharmaceutically acceptable excipient.

18. A method of inhibiting LpxC comprising contacting LpxC with a compound of claim 1, or a pharmaceutically acceptable salt thereof.

19. A method of treating a gram-negative bacterial infection in a patient in need thereof comprising administering to the patient the pharmaceutical composition of claim 17.

* * * * *